(12) United States Patent
Cowardin et al.

(10) Patent No.: US 10,196,453 B2
(45) Date of Patent: Feb. 5, 2019

(54) **COMPOSITIONS AND METHODS FOR TREATING *CLOSTRIDIUM DIFFICILE* INFECTION**

(71) Applicant: University of Virginia Patent Foundation, Charlottesville, VA (US)

(72) Inventors: Carrie Adeline Cowardin, St. Louis, MO (US); William A. Petri, Jr., Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 83 days.

(21) Appl. No.: 15/597,384

(22) Filed: May 17, 2017

(65) Prior Publication Data

US 2017/0334994 A1   Nov. 23, 2017

Related U.S. Application Data

(60) Provisional application No. 62/339,283, filed on May 20, 2016.

(51) Int. Cl.
    *A61K 39/00*     (2006.01)
    *C07K 16/28*     (2006.01)

(52) U.S. Cl.
    CPC .... *C07K 16/2896* (2013.01); *A61K 2039/505* (2013.01); *C07K 2317/76* (2013.01)

(58) Field of Classification Search
    CPC ............ C07K 2317/76; C07K 16/2803; C07K 16/2896; A61K 2039/505; A61K 2039/507
    See application file for complete search history.

(56) References Cited

U.S. PATENT DOCUMENTS

2014/0343256 A1* 11/2014 Kirschning ........ C07K 16/2896
                                                    530/387.3

OTHER PUBLICATIONS

Unger et al. Scientific Reports 5: Article No. 7850, published online Jan. 19, 2015.*
Savidge et al. Gastroenterology 125: 413-420, 2003.*
Kuehne, S. A. et al, "The role of toxin A and toxin B in Clostridium difficile infection", Nature 467, 711-713 (2010).
Lee, J. Y. et al, "Clostridium difficile toxin A promotes dendritic cell maturation and chemokine CXCL2 expression through p38, IKK, and the NF-kappaB signaling pathway", J. Mol. Med. Berl. Ger. 87, 169-180 (2009).
Stewart, D. B., Berg, A. & Hegarty, J., "Predicting Recurrence of C. difficile Colitis Using Bacterial Virulence Factors: Binary Toxin Is the Key", J. Gastrointest. Surg. 17, 118-125 (2013).
Hemmasi, S. et al, "Interaction of the Clostridium difficile Binary Toxin CDT and its Host Cell Receptor LSR", J. Biol. Chem. (2015). doi:10.1074/jbc.M115.650523.
Papatheodorou, P. et al, "Lipolysis-stimulated lipoprotein receptor (LSR) is the host receptor for the binary toxin Clostridium difficile transferase (CDT)", Proc. Natl. Acad. Sci. U. S. A. 108, 16422-16427 (2011).
Buonomo, E. L. et al, "Role of IL-23 signaling in Clostridium difficile Colitis", J. Infect. Dis. jit277 (2013). doi:10.1093/nfdis/jit277.
Morgan, J. E. & Beeson, P. B. "Experimental Observations on the Eosinopenia Induced by Acute Infection", Br. J. Exp. Pathol. 52, 214-220 (1971).
Fukushima, A., Yamaguchi, T., Ishida, W., Fukata, K. & Ueno, H, "TLR2 agonist ameliorates murine experimental allergic conjunctivitis by inducing CD4 positive T-cell apoptosis rather than by affecting the Th1/Th2 balance", Biochem. Biophys. Res. Commun. 339, 1048-1055 (2006).
Nawijn, M. C. et al, "TLR-2 Activation Induces Regulatory T Cells and Long-Term Suppression of Asthma Manifestations in Mice", PLoS ONE 8, e55307 (2013).
Carter, G. P. et al, "Binary Toxin Production in Clostridium difficile Is Regulated by CdtR, a LytTR Family Response Regulator", J. Bacteriol. 189, 7290-7301 (2007).
Mackin, K. E., Carter, G. P., Howarth, P., Rood, J. I. & Lyras, D., "Spo0A differentially regulates toxin production in evolutionarily diverse strains of Clostridium difficile", PloS One 8, e79666 (2013).

* cited by examiner

*Primary Examiner* — Sarvamangala Devi
(74) *Attorney, Agent, or Firm* — Rodney L. Sparks

(57) ABSTRACT

*Clostridium difficile* is the most common hospital acquired pathogen in the United States, and infection is in many cases fatal. Toxins A and B are its major virulence factors, but increasingly a third toxin may be present, known as *C. difficile* transferase (CDT). An ADP-ribosyltransferase that causes actin cytoskeletal disruption, CDT is typically produced by the major, hypervirulent strains and has been associated with more severe disease. It is disclosed herein that CDT enhances the virulence of two PCR-ribotype 027 strains in mice. The toxin induces pathogenic host inflammation via a novel Toll-like Receptor 2 (TLR2) dependent pathway, resulting in the suppression of a protective host eosinophilic response. Finally, it is disclosed that restoration of TLR2 deficient eosinophils is sufficient for protection from a strain producing CDT. These findings offer an explanation for the enhanced virulence of CDT-expressing *C. difficile* and demonstrate a mechanism by which this binary toxin subverts the host immune response.

Figure 1A:
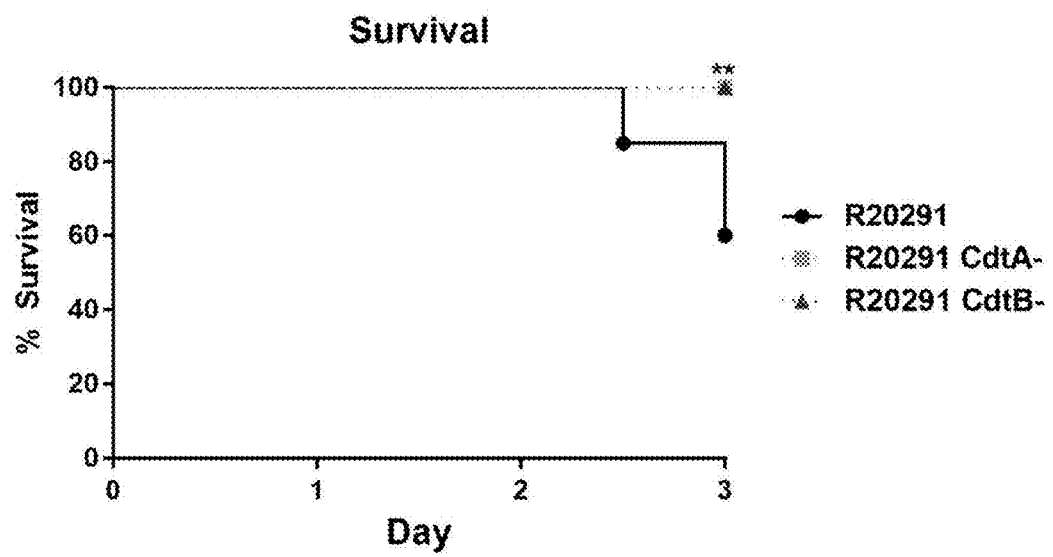
Figure 1B:
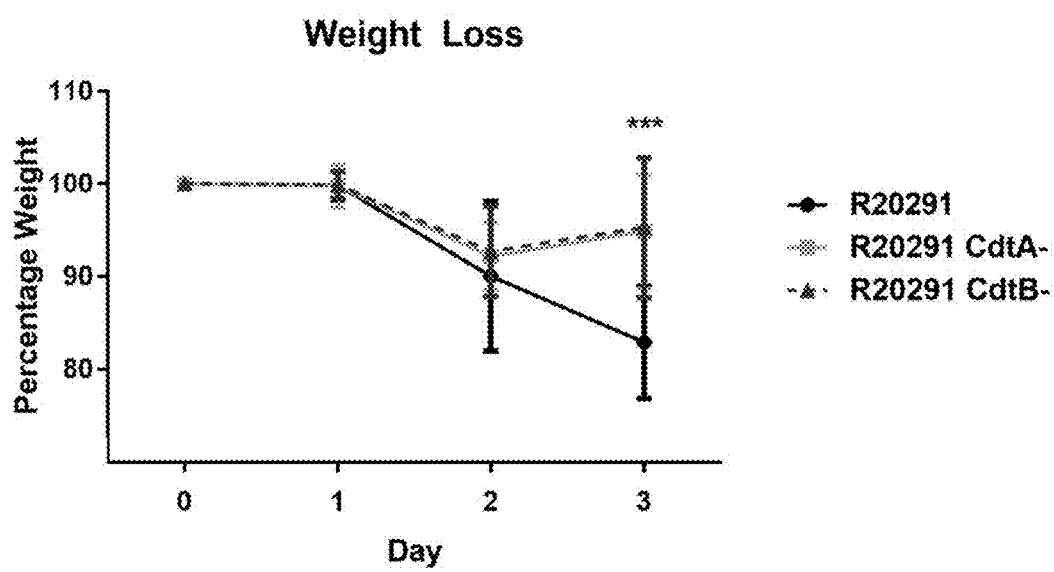

9 Claims, 25 Drawing Sheets
(5 of 25 Drawing Sheet(s) Filed in Color)

COMPOSITIONS AND METHODS FOR TREATING *CLOSTRIDIUM DIFFICILE* INFECTION

CROSS REFERENCE TO RELATED APPLICATIONS

This application claims priority under 35 U.S.C. § 119(e) to U.S. Provisional Application Ser. No. 62/339,283 filed May 20, 2016, the disclosure of which is incorporated by reference in its entirety herein.

STATEMENT REGARDING FEDERALLY SPONSORED RESEARCH OR DEVELOPMENT

This invention was made with government support under Grant Nos. AI124214, AI026649, and AI114734, awarded by The National Institutes of Health. The government has certain rights in the invention.

BACKGROUND

The Gram positive anaerobe *C. difficile* causes mild to severe antibiotic associated diarrhea, pseudomembranous colitis, toxic megacolon and death[1-2]. The Rho-glucosylating Toxins A and B (TcdA and TcdB) cause host cell death and profound inflammation and are required for symptomatic infection[3-7]. Production of the binary toxin CDT (*C. difficile* transferase) in addition to Toxins A and B by *C. difficile* is associated with higher mortality, increased peripheral white blood cell count, and elevated risk of recurrence in clinical studies[8-10]. CDT expressing strains have also become increasingly common over the last ten years, paralleling the overall increase in incidence and severity of CDI, and now account for up to 20% of isolates in the hospital setting[11-14]

CDT consists of two components which act cooperatively to intoxicate cells[14,15]. CDTb, the binding component of CDT, is produced as a precursor protein and requires proteolytic cleavage prior to intoxication. Following cleavage, CDTb associates with the lipolysis stimulated lipoprotein receptor, or LSR, which is required for intoxication[16,17]. This receptor is highly expressed within the liver, small intestine, colon and various other tissues, and is thought to be involved in the uptake and removal of lipoproteins and in the formation of tricellular tight junctions[18,19]. Following formation of the CDTb heptamer and binding to LSR, CDTa, the enzymatic component of CDT, then binds the CDTb heptamer. This complex is endocytosed, and endosomal acidification triggers insertion of the CDTb heptamer into the endosomal membrane through which CDTa is released into the cytoplasm[20]. CDTa then transfers an ADP-ribose moiety to globular actin, which then acts as a capping protein to prevent actin filament elongation. This results in collapse of the actin cytoskeleton, allowing the formation of microtubule protrusions on the surface of host cells which are thought to increase *C. difficile* adherence[21,22].

Although CDT production is associated with more severe disease, the role of CDT during infection is not well understood. In a hamster model of CDI, CDT was shown to enhance virulence in the presence of Toxin A, but not Toxin B. In humans, the intensity of the host inflammatory response is critical in determining disease outcome, and in murine models, innate IL-23 production is detrimental during infection[23-26]. Toxins A and B shift the immune response towards this pathogenic inflammatory state by inducing IL-1β secretion via activation of the inflammasome[26,27].

There is a long felt need in the art for compositions and methods useful for treating or preventing *C. difficile* infection. The present invention satisfies these needs.

SUMMARY OF THE INVENTION

Without wishing to be bound by any particular theory, it is hypothesized herein that CDT may play an additional role during infection by influencing host inflammatory signaling. The present invention is based on the unexpected discovery disclosed herein that harmful effects of CDT are mediated via Toll-Like Receptor 2 (TLR2) signaling.

In order to investigate the role of CDT during disease, the present application utilized isogenic CDT mutants of two distinct PCR-ribotype 027 strains in a mouse model of *C. difficile* colitis (R20291 and M7404). While both strains are human isolates that express Toxins A and B as well as CDT, R20291 was originally isolated from an outbreak in the United Kingdom while M7404 originated in Canada[28,29]. It is disclosed herein that CDT is a true virulence factor capable of enhancing virulence in conjunction with Toxins A and B. Unexpectedly, it was found that CDT increased pathogenic host inflammation via a novel Toll-like Receptor 2 dependent pathway, which was required for CDT suppression of a protective host eosinophilic response during infection. The present application discloses for the first time that TLR2 is a receptor for CDT. Therefore, the present invention encompasses, inter alia, compositions and methods for inhibiting the effects of CDT by inhibiting its interaction with TLR2 or by blocking the activity of TLR2.

In one embodiment, the present invention provides compositions and methods for preventing or treating *C. difficile* infection comprising administering inhibitors of Toll-like Receptor 2 (TLR2) and its dependent pathway in subjects infected with *C. difficile* strains that produce CDT. In one aspect, inhibitors of TLR2 are administered to a subject in need thereof. Inhibitors include, but are not limited to, those that inhibit levels, expression, and activity of TLR2. Inhibition of activity can also include inhibiting its downstream signaling and pathways. The inhibitors can act directly on TLR2 or can, for example, inhibit its interaction with its ligand. The inhibitors include, but are not limited to, antibodies, fragments of antibodies, humanized antibodies, monoclonal antibodies, aptamers, phylomers, antisense oligonucleotides, nucleic acids, siRNA, proteins, other biologics, and drugs.

In one embodiment, the inhibitor binds to TLR2. In one aspect, it prevents TLR2 from interacting with its ligand. In one aspect, it inhibits TLR2 activity.

The compositions and methods of the invention are useful for inhibiting the effects of CDT, including, reducing its ability to stimulate host inflammatory signaling, inhibiting its enhancement of virulence of certain *C. diff.* strains, inhibiting its suppression of protective colonic eosinophilia, and inhibiting its promotion of apoptosis of eosinophils.

In one embodiment, an inhibitor of TLR2 is administered in combination with an agent that binds with CDT, wherein the agent that binds to CDT inhibits the interaction of CDT with its target or inhibits CDT activity.

In one embodiment, an inhibitor of CDT activity is administered. The inhibitor can include, but is not limited to, antibodies, vaccines, and chemicals.

In one embodiment, inhibiting CDT inhibits its ability to increase virulence of certain *C. difficile* strains.

In one embodiment, the present invention provides for the use of TLR2-deficient eosinophils to treat or prevent *C. difficile* infection. TLR2-deficient eosinophils can be prepared, for example, using gene-editing technology. Stem or progenitor cells with the ability to give rise to eosinophils can be subjected to gene editing to produce TLR2-deficient cells and then expanded/differentiated to produce sufficient cells for administering to the subject or can be administered such that they will expand and/or differentiate once administered. In one aspect, eosinophils can be subjected to the gene editing. In one aspect, the cells are derived from the subject.

In one embodiment, C. difficile infection can be prevented or treated using a combination treatment comprising administration of TLR2-deficient eosinophils or TLR2-deficient eosinophil precursors and at least one inhibitor of TLR2. In one embodiment, an inhibitor of CDT can also be administered.

Figure 1C:
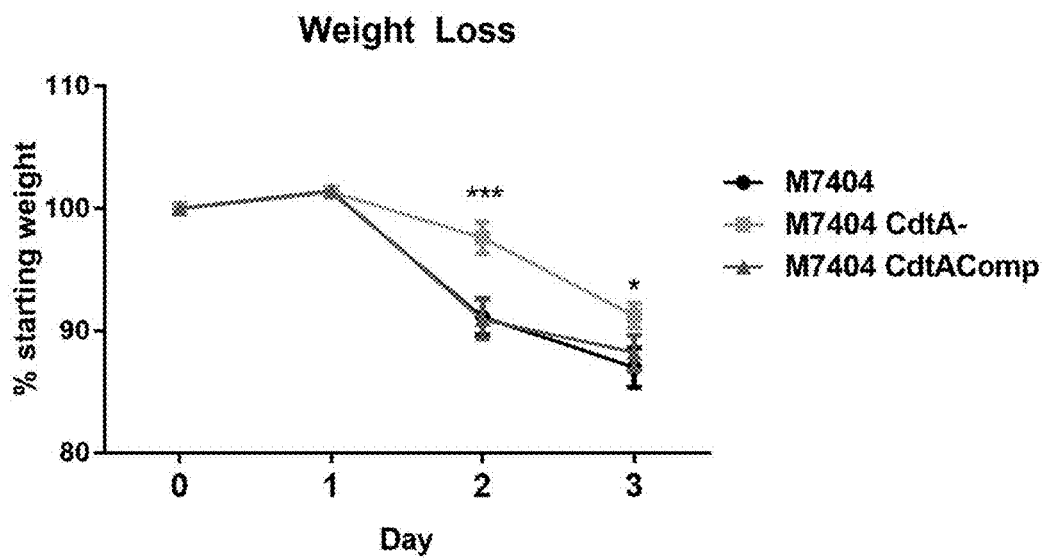
Figure 1D:
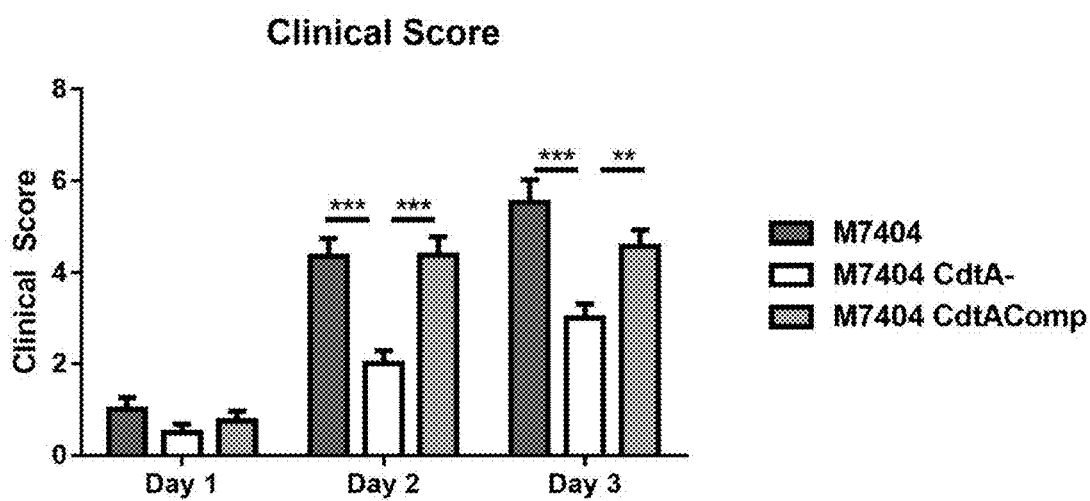

The present invention provides antibodies useful for identifying and monitoring TLR2 expression levels and expression. The present invention provides antibodies useful for inhibiting CDT induced activity of TLR2 and for inhibiting TLR2. There are multiple commercial sources for these antibodies including Invivogen, Abcam, ThermoFisher, and R&D Systems. Useful Invivogen antibodies include: 1) Anti-hTLR2-IgA Human TLR2 Detection and Neutralizing antibody—Monoclonal Human IgA2 (clone B4H2, catalog code maba2-htlr2); 2) Anti-mTLR2-IgG Mouse TLR2 Neutralizing antibody—Monoclonal Mouse IgG2a (clone C9A12; catalog code mabg-mtlr2); 3) MAb-hTLR2 Human TLR2 Detection antibody—Monoclonal Mouse IgG2a (TL2.1); 4) MAb-mTLR2 Mouse TLR2 Detection and Neutralizing antibody—Monoclonal Mouse IgG1 (clone T2.5; catalog code mab-mtlr2); and 5) PAb-hTLR2 Human TLR2 Neutralizing antibody—Polyclonal Rat IgG (catalog code pab-hstlr2). Other useful antibodies directed against TLR2 include, but are not limited to, human TLR2 antibody mAb2616 (R&D Systems). Useful antibodies from Abcam include, but are not limited to, mouse monoclonal Anti-TLR2 antibody [TL2.1], product code ab9100, reactive against multiple species, including humans and is a neutralizing antibody; Anti-TLR2 antibody [EPNCIR133] product code ab108998, rabbit monoclonal with reactivity against multiple species, including humans; Anti-TLR2 antibody [T2.5], product code ab16894, mouse monoclonal cross reactive with multiple species, including humans; Anti-TLR2 antibody (product code ab213676), rabbit polyclonal cross reactive with multiple species, including humans; Anti-TLR2 antibody (product code ab191458), rabbit polyclonal cross reactive with multiple species, including humans; Anti-TLR2 antibody [T2.5] (FITC) (product code ab59711), mouse monoclonal cross reactive with multiple species, including humans; Anti-TLR2 antibody (product code ab1655), goat polyclonal directed against human TLR2; Anti-TLR2 antibody [TL2.1] (Biotin) (product code ab9101), mouse monoclonal directed against multiple species, including humans; Anti-TLR2 antibody [TL2.1] (FITC) (product code ab13553), mouse monoclonal against multiple species, including human; Anti-TLR2 antibody [TL2.1] (Phycoerythrin) (ab171568). Useful antibodies from ThermoFisher include, but are not limited to neutralizing mouse CD282 (TLR2) monoclonal antibody (TL2.1) reactive with human, catalog no. 16-9922-82 or -83; and mouse IgG2a neutralizing TLR2 monoclonal antibody (TL2.1), catalog no. MA5-16200, cross-reactive with human. For purposes of neutralizing or inhibiting TLR2 activity, only antibodies with such properties will be used.

Clinical doses of antibodies are disclosed herein and are also known in the art. Doses can vary depending on the age, sex, weight, body surface area (BSA), and health of the subject, as well as the specific disease, injury, or disorder being treated. Additionally, a higher dose may be used in some cases where an immediate effect is needed, such as when trying to prevent or treat something like sepsis or lethal shock-like syndrome. Doses can be administered as a unit dose or the dose can be based on criteria such as those describe above for body weight, etc. Cartron et al. (Blood, 2002, 99:754-758) used Rituximab in humans as a total of four 375 mg/$m^2$ doses by intravenous infusion spread out over several weeks. Maini et al. (Clinical Science, 1998, 41:9:1552-1563) used a monoclonal anti-tumor necrosis-factor $\alpha$ antibody (infliximab/Remicade) at 1, 3, or 10 mg/kg delivered intravenously in patients with rheumatoid arthritis and administered it at 0, 2, 6, 10 and 14 weeks. Single-dose administration of anti-interleukin-13 antibody (tralokinumab) at 300 mg in adolescents with asthma was well-tolerated (Baverel et al., Br. J. Clin. Pharmacol., 2015, 80:6:1337-1349). The anti-PDGFR antibody Imatinib has been used at varying doses in humans, including, for example, at daily doses of 400 mg, 600 mg and 800 mg (Michael et al., Cancer Chemother. Pharmacol., 2013, 71:2:321-330). Bebb et al. (Cancer Chemother. Pharmacol., 2011, 67:4:837-845) used the anti-EGFR monoclonal antibody nimotuzumab in humans at doses of 100 mg, 200 mg and 400 mg weekly and stated that it has been shown to be well tolerated at doses of 50-800 mg. The T2.5 monoclonal antibody that is antagonistic to TLR2 has been used to prevent lethal shock-like syndrome and it increased survival with administered 1 hour before or up to 3 hours after infection (Meng et al, J. Clin. Invest., 2004, 113:1473). It was effective at 40 mg/kg for this short-term treatment used for preventing or treating shock-like syndrome at the time of infection and pre-treatment with 0.5 mg or 1.0 mg were effective. Intracellular antibodies have also been used to block translocation of TLR2. Spiller et al. (J. Exp. Med., 2008, 205:8:1747-1754) used an anti-TLR2 antibody (T2.5) at 30 mg/kg to prevent or treat sepsis after LPS injection.

In one embodiment, a therapeutic dose of an antibody of the invention, including, but not limited to, monoclonal antibodies, chimeric antibodies, humanized antibodies, various kinds of fragments, and biologically active homologs and fragments thereof, is from about 0.1 mg/dose to about 5,000 mg/dose or from about 0.2 mg/dose to about 1,000 mg/dose. Doses can also be administered based on body weight, for example at a dosage ranging from about 0.01 mg/kg to about 1,000 mg/kg body weight or from about 0.1 to about 500 mg/kg.

Additional therapeutic agents can also be administered as determined by one of ordinary skill in the art, for example, drugs, antibiotics, probiotics and pre-biotics can be administered.

The present invention further encompasses kits for treating subjects in need thereof.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1, comprising FIG. 1A-F: CDT expression enhances the virulence of PCR-ribotype 027 *C. difficile* in a murine model of infection.

(FIG. 1A-B) 8 week old C57BL/6J mice underwent an antibiotic regimen prior to infection with $10^7$ CFU of vegetative *C. difficile* strain R20291 or the isogenic mutants R20291 CdtA− or R20291 CdtB− (data shown combined from two independent experiments, n=15). (FIG. 1A) Animals were monitored for survival and (FIG. 1 B) weight loss. (FIG. 1C-D) Mice were treated with the same antibiotic regimen before infection with $2\times10^5$ CFU of M7404, M7404 CdtA− or M7404 CdtAComp (data shown combined from two independent experiments (n=16). (FIG. 1C) Animals were monitored for weight loss and (FIG. 1D) clinical score. (FIG. 1E-F) Mice were sacrificed on day 2 of infection and cecal sections were isolated and fixed in Bouin's solution for 18 hours before undergoing paraffin embedding, sectioning and haematoxylin & eosin staining. (FIG. 1F) Samples were scored blinded by 3 independent observers. (FIG. 1E) data shown are representative or (FIG. 1F) combined from two independent experiments (n=13). *=p value <0.05, =p value <0.01, *=p value <0.001 by Kaplan-Meier curve (FIG. 1A), two-tailed t-test (FIG. 1B-C) and Mann-Whitney test (FIG. 1 D,F). NS=not significant. Error bars shown represent S.D. (FIG. 1B,C) or S.E.M. (FIG. 1D,F).

FIG. 2, comprising FIG. 2A-G: CDT promotes host inflammatory signaling.

Figure 2A:
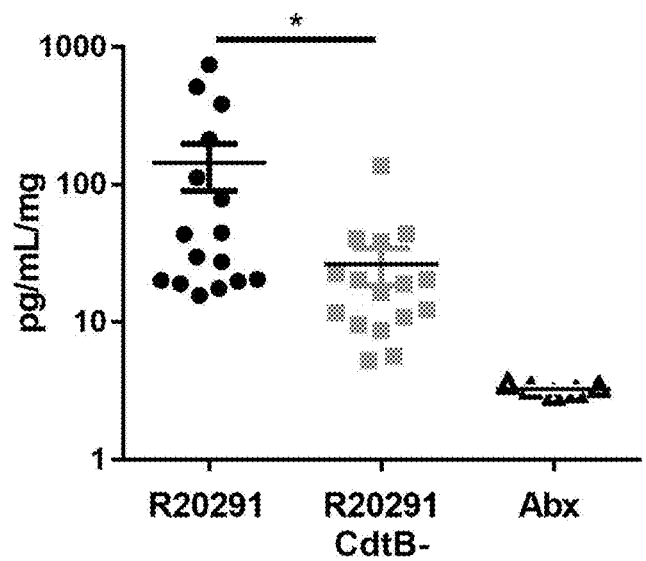
Figure 2B:
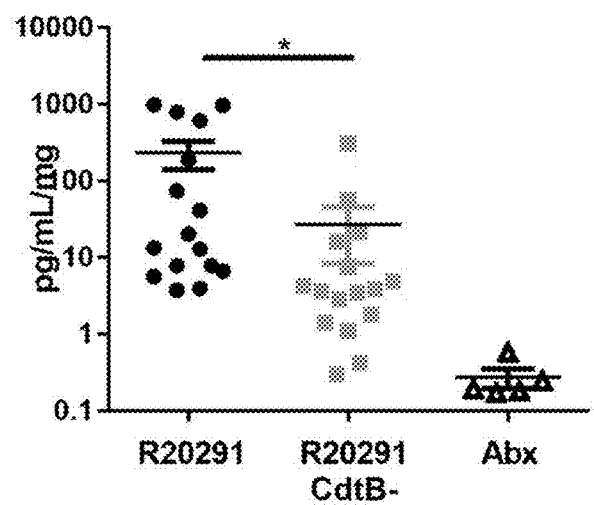
Figure 2C:
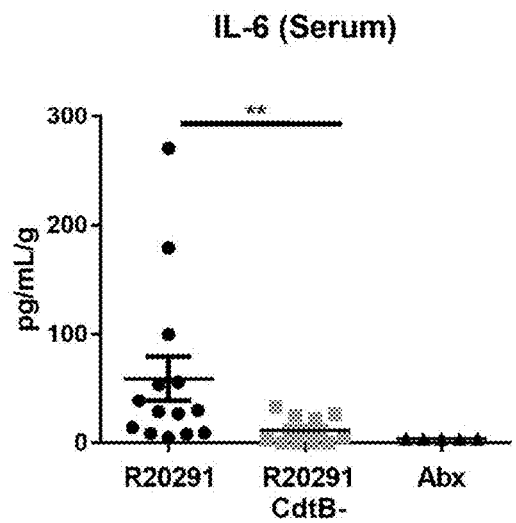
Figure 2D:
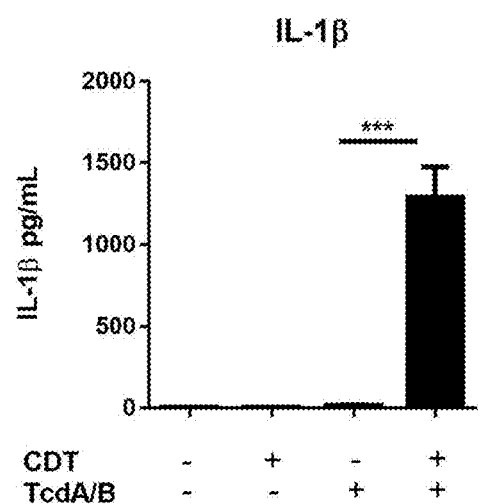
Figure 2E:
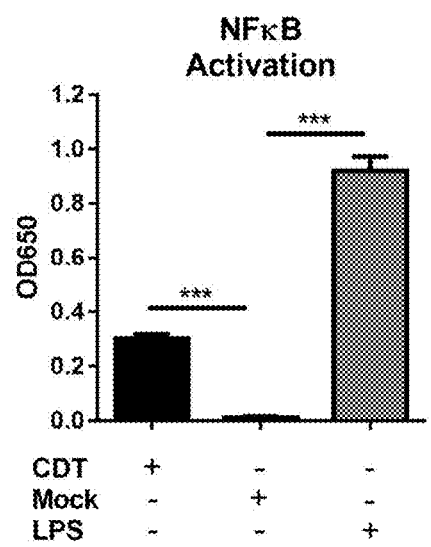
Figure 2F:
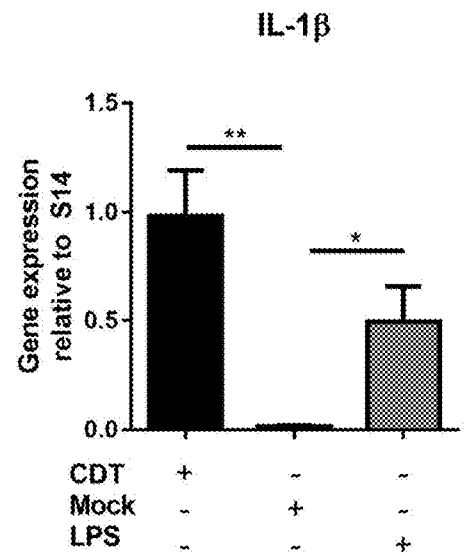
Figure 2G:
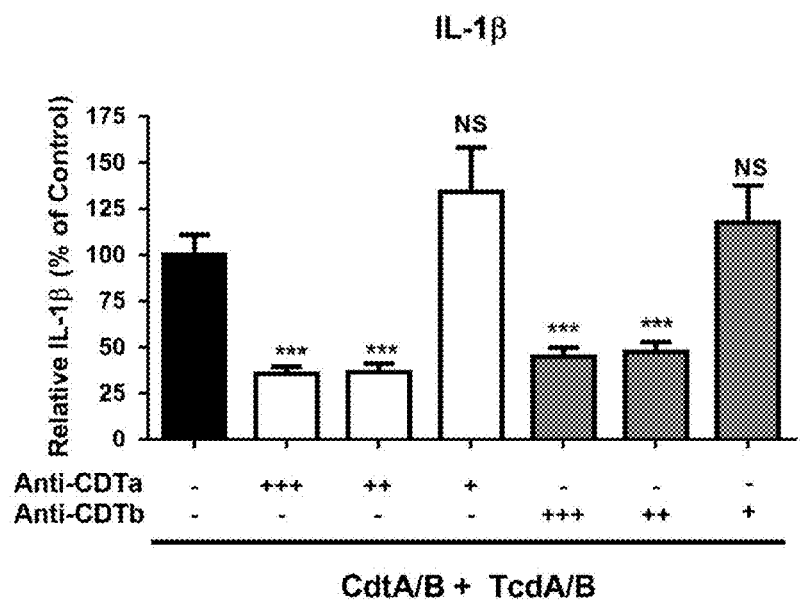

(FIG. 2A-B) Mice infected with the indicated strain or uninfected and treated with antibiotics only (Abx) were sacrificed on day 3 of infection and cecal cytokines assessed by lysing whole cecal sections and quantifying protein via ELISA (data combined from two independent experiments, shown normalized to total protein concentration, n=16). (FIG. 2C) Serum IL-6 was measured via ELISA at the same time point (n=14). (FIG. 2D) Bone marrow derived dendritic cells were treated with 200 ng/mL purified CDTa and CDTb (CDT) or 2 ng/mL Toxin A and 2 ng/mL Toxin B (TcdA/B) for 24 hours. Secreted IL-1β was measured by ELISA. (FIG. 2E) NFκB activation was detected in a Raw Blue NFκB reporter cells by measuring Secreted Embryonic Alkaline Phosphatase (SEAP) in the culture media. (FIG. 2F) BMDCs were treated with 200 ng/mL CDTa and 200 ng/mL CDTb or with 100 ng/mL LPS as a positive control for 8 hours. Pro-IL-1β gene expression was assessed by qRT-PCR and is shown normalized to S14 housekeeping gene. (FIG. 2G) BMDCs were treated with 200 ng/mL CDTa and 200 ng/mL CDTb plus 2 ng/mL Toxin A and 2 ng/mL Toxin B in combination with decreasing amounts of anti-CDTa nanobody or anti-CDTb nanobody as indicated. +++=200 ng/mL, ++=20 ng/mL, +=2 ng/mL. Secreted IL-1β was measured by ELISA. Data shown combined from 3 independent experiments with 3 replicates each (FIG. 2D-G). *=p value <0.05, =p value <0.01, *=p value <0.001 by Welch's unequal variance t-test (FIG. 2A-F) or Mann-Whitney test (FIG. 2G). NS=not significant. Error bars shown represent S.E.M.

FIG. 3, comprising FIG. 3A-E: CDT production suppresses protective colonic eosinophilia.

Figure 3A:
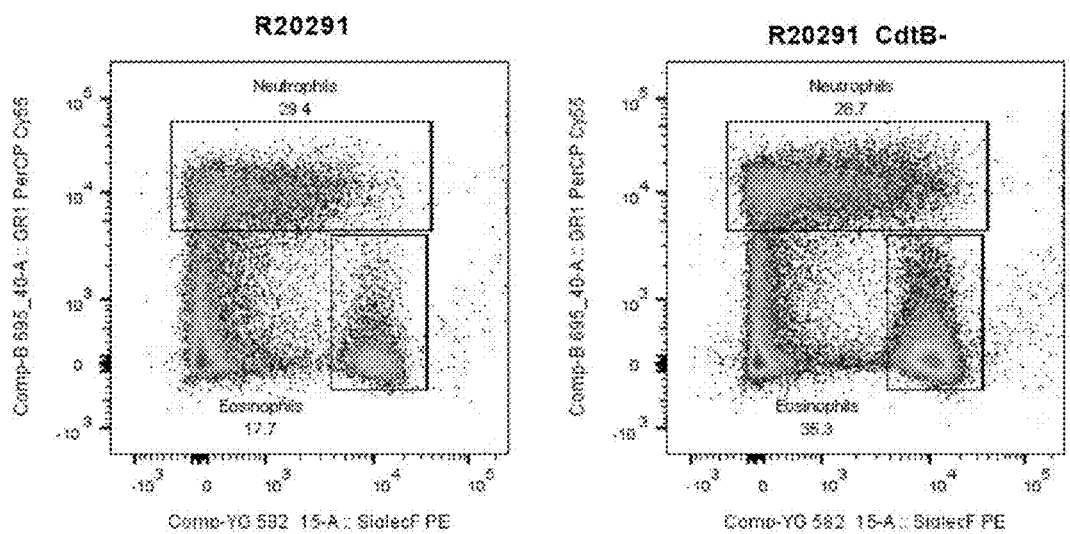
Figure 3B:
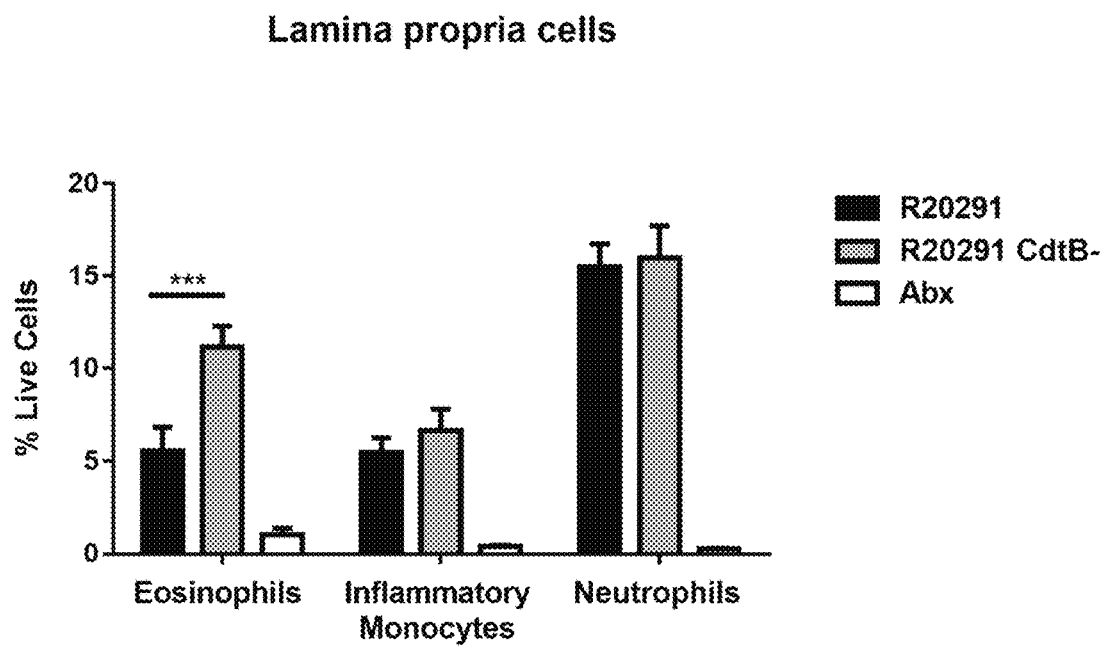
Figure 3C:
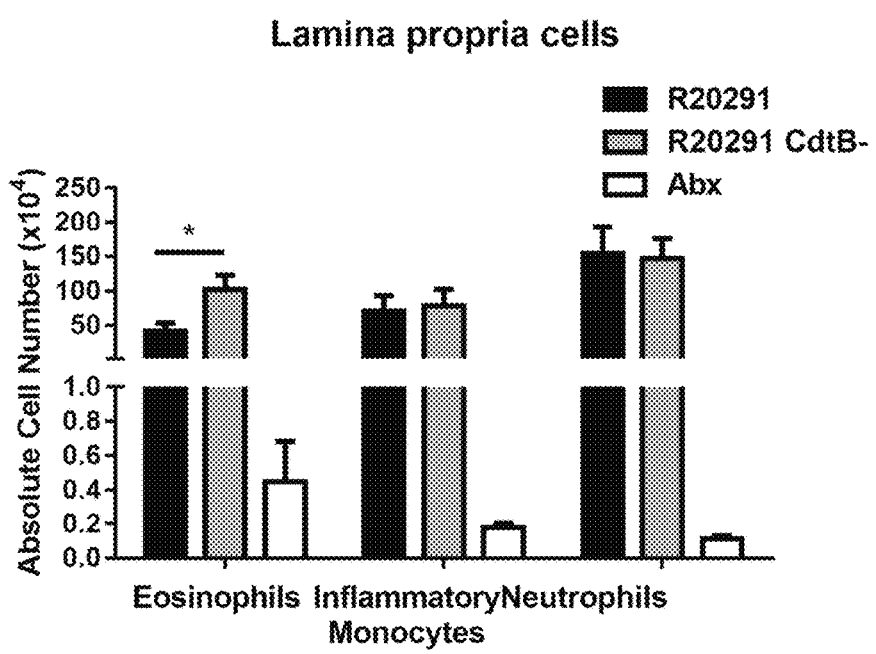
Figure 3D:
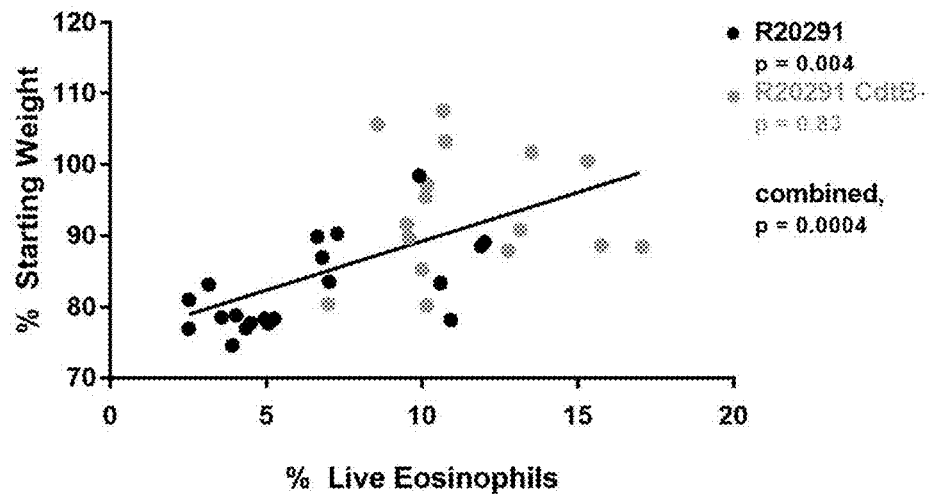
Figure 3E:
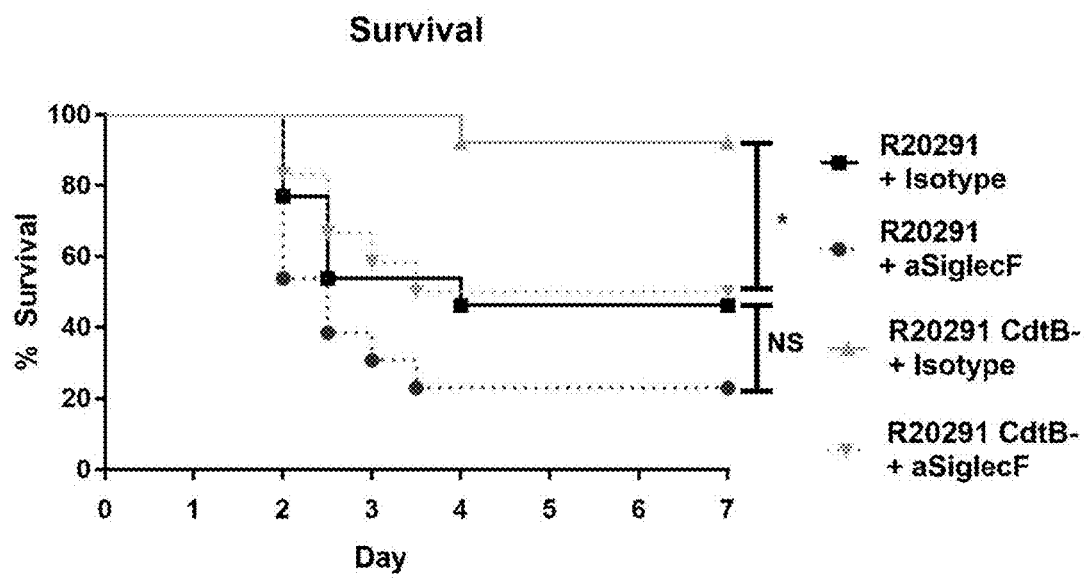

(FIG. 3A) Mice infected with the indicated strain, or uninfected and treated with antibiotics only (Abx) were sacrificed on day 3. Colon tissue was isolated and processed to a single cell suspension and stained for flow cytometry. Representative flow plots depicting neutrophils and eosinophils are shown (two independent experiments, n=10). (FIG. 3B-C) Eosinophils (CD45$^+$ CD11b$^+$ SiglecF$^+$), monocytes (CD45$^+$ CD11b$^+$ Ly6C$^{hi}$) and neutrophils (CD45$^+$ CD11b$^+$ Ly6G$^+$) were quantified. All three cell types are significantly elevated in both infected groups compared to Abx treated controls (data shown combined from two independent experiments, n=10). (FIG. 3D) Weight loss and percentage live colon eosinophils were compared using data combined from four independent experiments (n=17). (FIG. 3E) Colonic eosinophils were depleted using 40 ug of an anti-SiglecF targeted antibody or an isotype control antibody one day prior and one day following infection with *C. difficile*. Animals were monitored for clinical symptoms and humanely euthanized when required. Data shown combined from two independent experiments (n=13). *=p value <0.05, =p value <0.01, *=p value <0.001 by Mann-Whitney test (FIG. 3B-C), linear regression (FIG. 3D) or Kaplan-Meier curve (FIG. 3E). NS=not significant. Error bars shown represent S.E.M.

FIG. 4, comprising FIG. 4A-F: CDT production by *C. difficile* promotes eosinophil apoptosis.

Figure 4A:
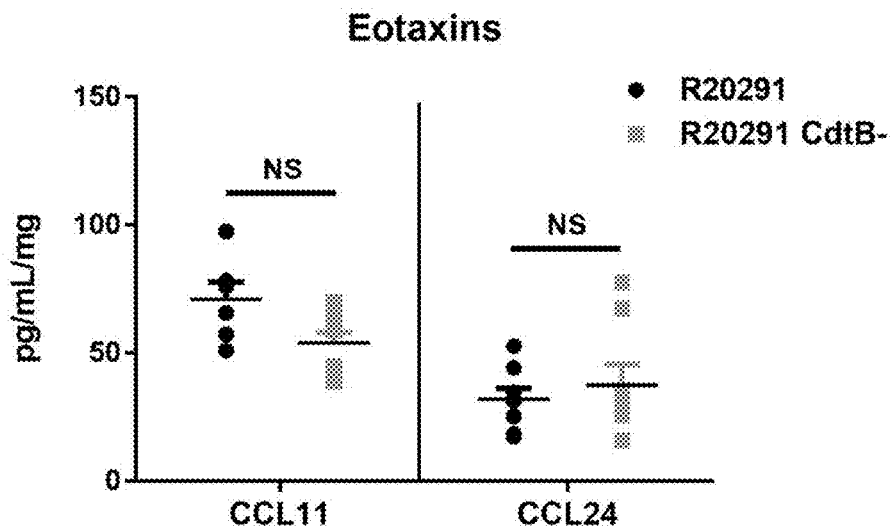
Figure 4B:
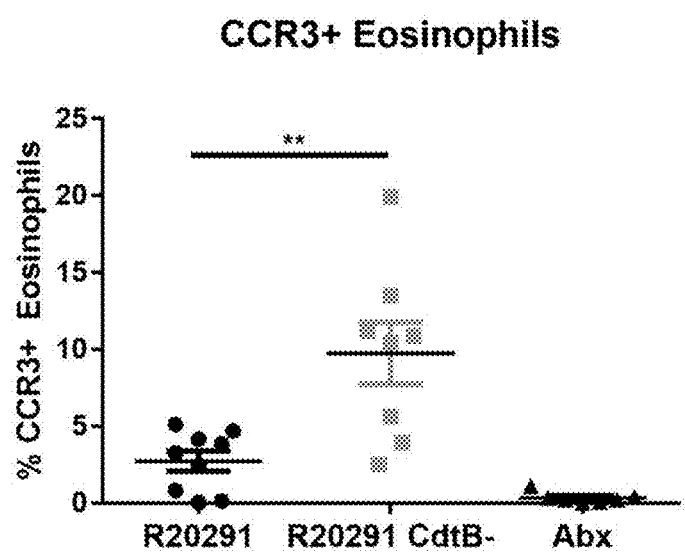
Figure 4C:
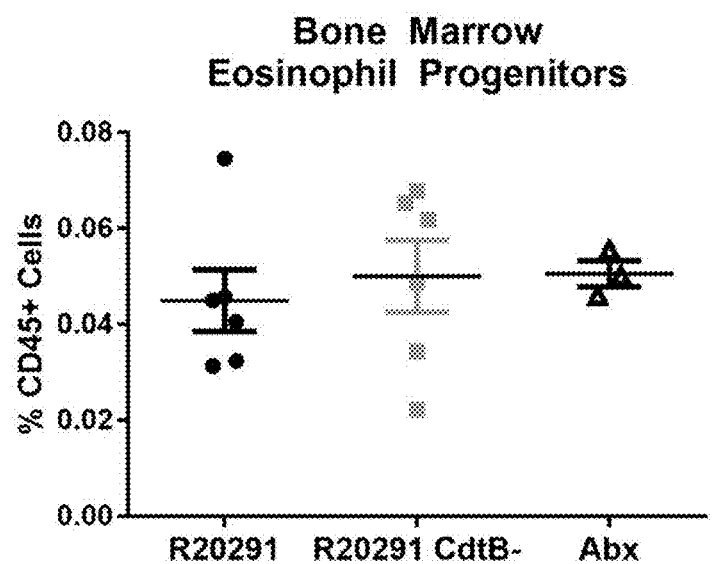

(FIG. 4A) Mice infected with the indicated strain, or uninfected and treated with antibiotics (Abx) were sacrificed on day 3. Cecal eotaxin levels were assessed by lysing whole cecal sections and quantifying protein via ELISA (data combined from two independent experiments, shown normalized to total protein concentration, n=16). (FIG. 4B) Colon tissue was isolated and processed to a single cell suspension and stained for flow cytometry. CCR3 staining on eosinophils was assessed by first gating on total eosinophils (identified as CD45$^+$ CD11b$^+$ SiglecF$^+$ SSC$^{hi}$ cells) (data shown are representative of 2 independent experiments, n=8). (FIG. 4C-D) Mice were sacrificed on day 3 and bone marrow harvested for flow cytometry. Eosinophil progenitors were identified as Lin− CD34+ Sca-1$^-$ IL-5Rα$^+$ cKit$^{int}$ cells by flow cytometry. Mature bone marrow eosinophils were quantified as CD45$^+$ CD11b$^+$ SiglecF$^+$ SSC$^{hi}$ cells (data shown combined from 2 independent experiments, n=6). (FIG. 4E-F) Blood eosinophils were assessed on day 3 of infection by flow cytometry following cardiac puncture, red blood cell lysis, and staining. Live eosinophils were identified at CD45$^+$ CD11b$^+$ SiglecF$^+$ Live dead$^{neg}$ and apoptotic eosinophils identified as CD45$^+$ CD11b$^+$ SiglecF$^+$ Annexin V$^+$ Live dead$_{neg}$ cells. Data shown combined from two independent experiments. (n=7) *=p value <0.05, =p value <0.01, *=p value <0.001 by Mann-Whitney test (FIG. 4A, C-D, F) or Welch's unequal variance t-test (FIG. 4B, E). NS=not significant. Error bars shown represent S.E.M.

FIG. 5, comprising FIG. 5A-F: TLR2 mediates CDT recognition and is required for eosinophil suppression.

Figure 5A:
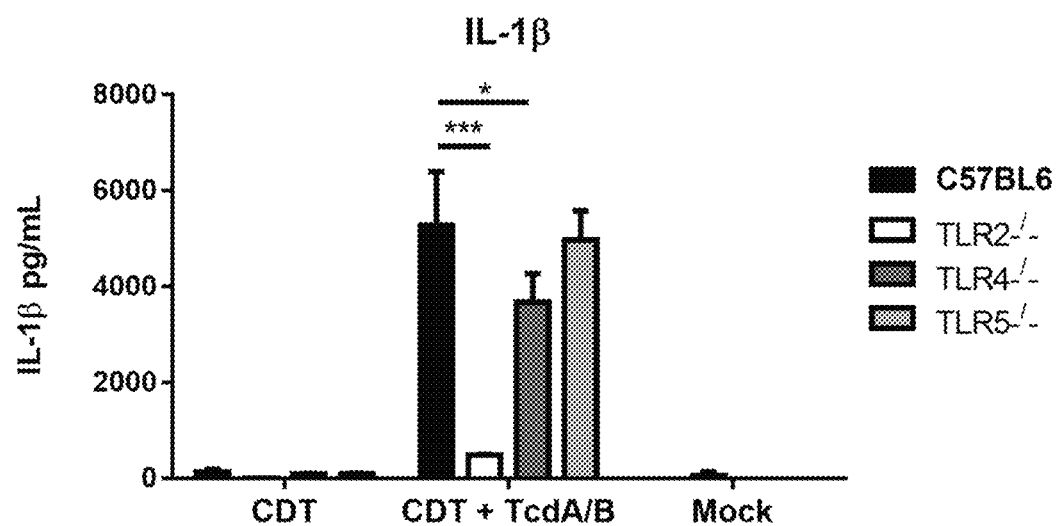
Figure 5B:
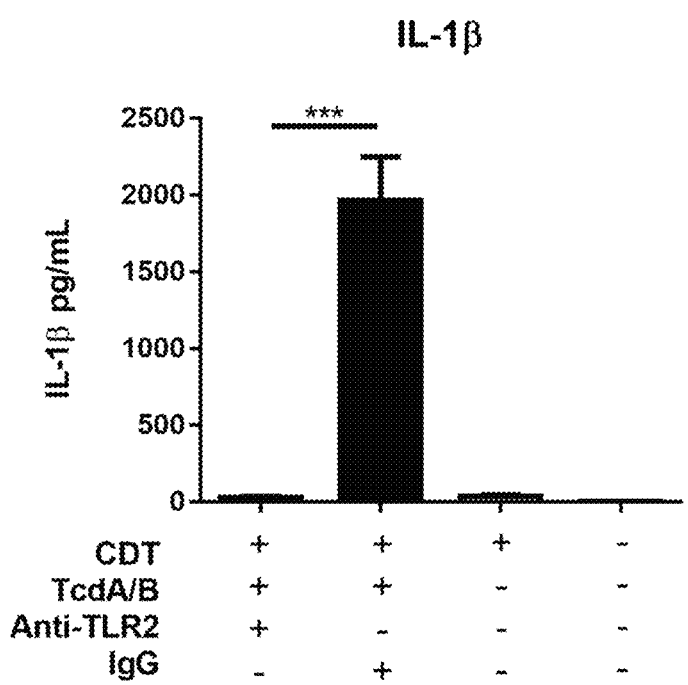
Figure 5C:
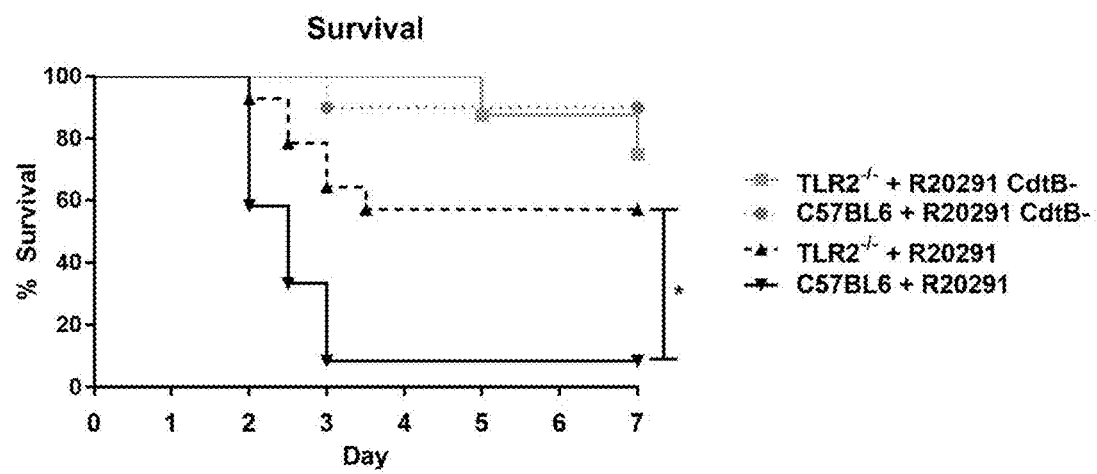

(FIG. 5A) BMDCs were generated from TLR2$^{-/-}$, TLR4$^{-/-}$, and TLR5$^{-/-}$ mice before treatment with 200 ng/mL CDTa and 200 ng/mL CDTb (CDT) and 2 ng/mL Toxin A and 2 ng/mL Toxin B (TcdA/B) for 24 hours. IL-1β secretion was assessed by ELISA. (FIG. 5B) BMDCs were treated with 200 ng/mL CDTa and 200 ng/mL CDTb (CDT) and 2 ng/mL Toxin A and 2 ng/mL Toxin B (TcdA/B) for 24 hours in the presence of a TLR2 neutralizing antibody (Invivogen; clone C9A12) or an isotype control. IL-1β was assessed by ELISA. Data shown combined from three independent experiments of 3 replicates each (FIG. 5A-B). (FIG. 5C) 8 week old TLR2 knockout mice or C57BL/6J mice were infected with R20291 or R20291 CdtB− and monitored for survival (data combined from two independent experiments, n=14). (FIG. 5D) Mice were sacrificed on day 3 of infection and colonic eosinophils (CD45$^+$ CD11b$^+$ SiglecF$^+$ SSC$^{hi}$) were measured by flow cytometry following tissue processing and staining (data combined from two independent experiments, n=8). (FIG. 5E) C57BL/6 mice received $4\times10^5$ TLR2$^{-/-}$ or B6 bone marrow-derived eosinophils (TLR2$^{-/-}$ Eo or B6 Eo) via IP injection one day prior and for 3 subsequent days following infection with R20291 or R20291 CdtB−. Mice were monitored daily for survival (data combined from two independent experiments, n=13). (FIG. 5F) BM Eos were incubated for 8 hours with 200 ng/mL CDTa and 200 ng/mL CDTb in the presence or absence of anti-TLR2 neutralizing antibody (aTLR2) or anti-CDT neutralizing nanobody (aCDT). Eosinophils were stained with Live dead or Annexin V and cell death was assessed by flow cytometry, data shown are representative of 3 independent experiments assayed in duplicate. *=p value <0.05, =p value <0.01, *=p value <0.001 by Mann-Whitney test (FIG. 5A), Welch's unequal variance t-test (FIG. 5B, D, F) or Kaplan-Meier Analysis (FIG. 5C, E). NS=not significant. Error bars shown represent S.E.M.

FIG. 6, comprising FIG. 6A-G (also referred to as Supplemental FIG. 1): *C. difficile* burden, Toxins A and B, translocation of commensals and histology scoring. (FIG. 6A-C) 8 week old C57BL/6J mice underwent an antibiotic regimen prior to infection with $10^7$ CFU of vegetative *C. difficile* strain R20291 or the isogenic mutant lacking the binding domain of CDT (R20291 CdtB−) (data shown combined from three independent experiments, n=24). (FIG. 6D) Mice were sacrificed on day 2 of infection and cecal sections were fixed in Bouin's solution for 18 hours before undergoing paraffin embedding, sectioning and hematoxylin & eosin staining. Samples were scored blinded based on 5 parameters (submucosal edema, inflammatory infiltrate, epithelial disruption, luminal exudate and mucosal thickening). (FIG. 6E) Mice were sacrificed on day 3 and Toxins A and B in the cecal contents were assessed via ELISA. (FIG. 6F) Cecal *C. difficile* burden was enumerated anaerobically on Brain-Heart Infusion agar. (FIG. 6G) Total liver bacterial burden was determined by plating liver homogenate on non-selective BHI and incubating aerobically overnight. Data shown combined from two independent experiments (n=13 in FIG. 6D, n=15 in FIG. 6E-F, and n=7 in FIG. 6G). *=p value <0.05, =p value <0.01, *=p value <0.001 by Kaplan-Meier Analysis (FIG. 6A) or Mann-Whitney test (FIG. 6B-G). NS=not significant. Error bars shown represent S.D. (FIG. 6B) or S.E.M. (FIG. 6C-G).

Figure 7A:
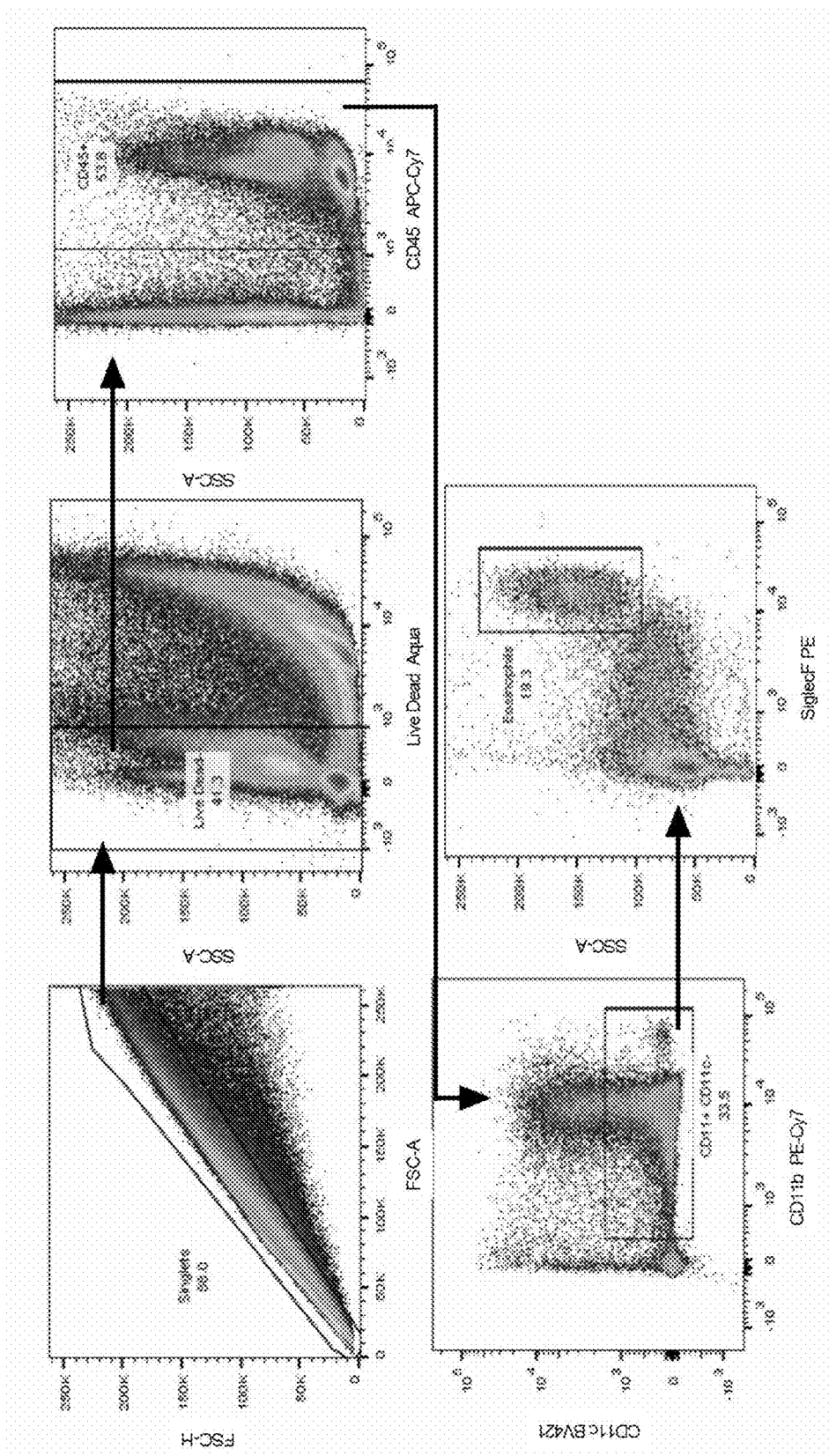
Figure 7B:
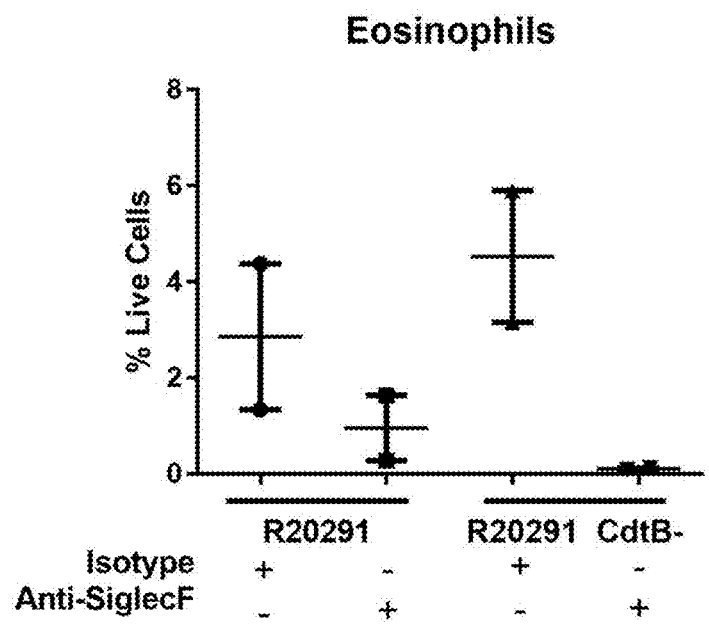
Figure 7C:
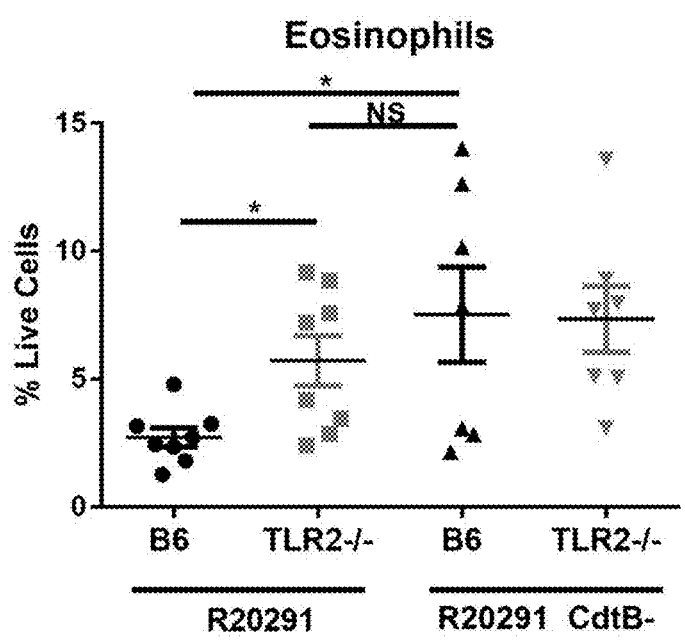

FIG. 7, comprising FIG. 7A-C (also referred to as Supplemental FIG. 2): Eosinophil gating strategy and depletion with anti-SiglecF. (FIG. 7A) Mice were sacrificed on day 3 of infection and colonic eosinophils were measured by flow cytometry following tissue processing and staining. The gating strategy identified singlets, Live dead negative cells, CD45+ cells, CD11b+ CD11c− and SiglecF+ side scatter high populations as eosinophils. Data shown are representative of 2 independent experiments. (FIG. 7B) Eosinophil depletion was quantified on day 3 of infection in mice treated with anti-SiglecF or an isotype control antibody (two IP injections of 40 ug each on the day before and the day following infection) infected with R20291 or R20291 CdtB− (n=2). (FIG. 7C) TLR2$^{−/−}$ mice or C57BL/6J mice were infected with wild-type R20291 or the isogenic CDT mutant R20291 CdtB− and were sacrificed on day 3 of infection. Colonic eosinophils (CD45$^+$ CD11b$^+$ SiglecF$^+$ SSC$^{hi}$) were measured by flow cytometry following tissue processing and staining (data shown as a percent of live cells, combined from two independent experiments, n=8). *=p value <0.05, =p value <0.01, *=p value <0.001 by Welch's unequal variance t-test (FIG. 7C). NS=not significant. Error bars shown represent S.E.M.

Figure 8A:
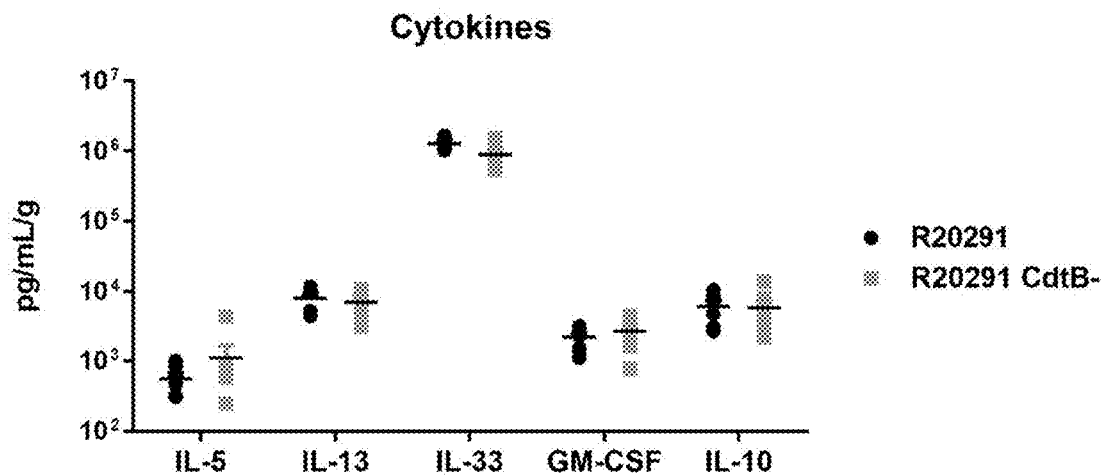
Figure 8B:
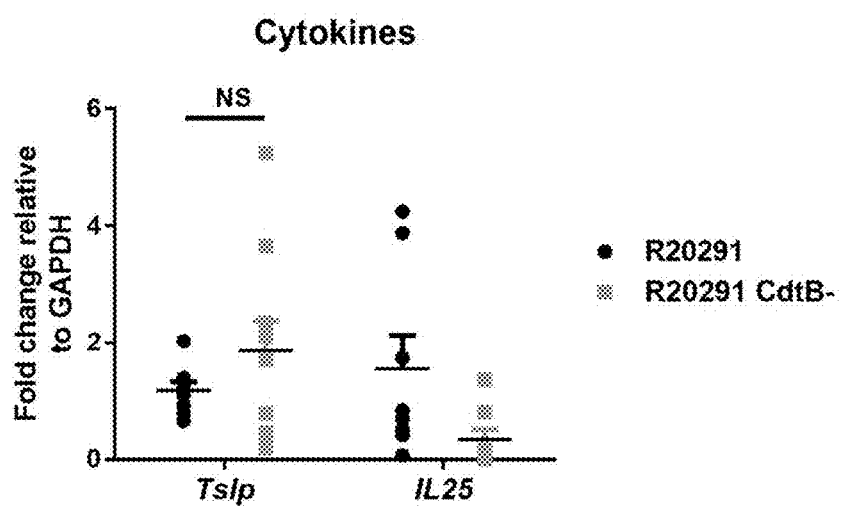
Figure 8C:
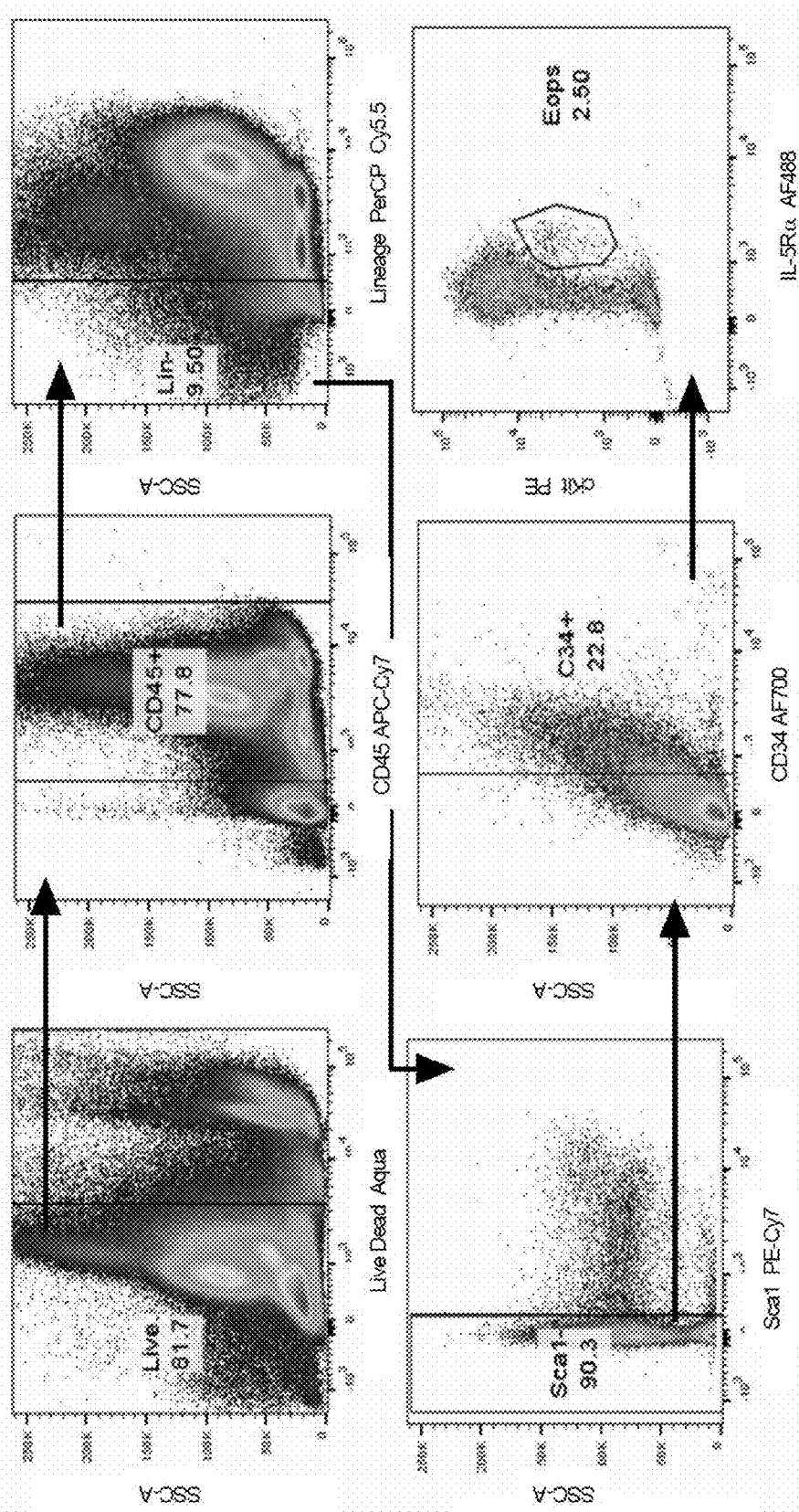
Figure 9A:
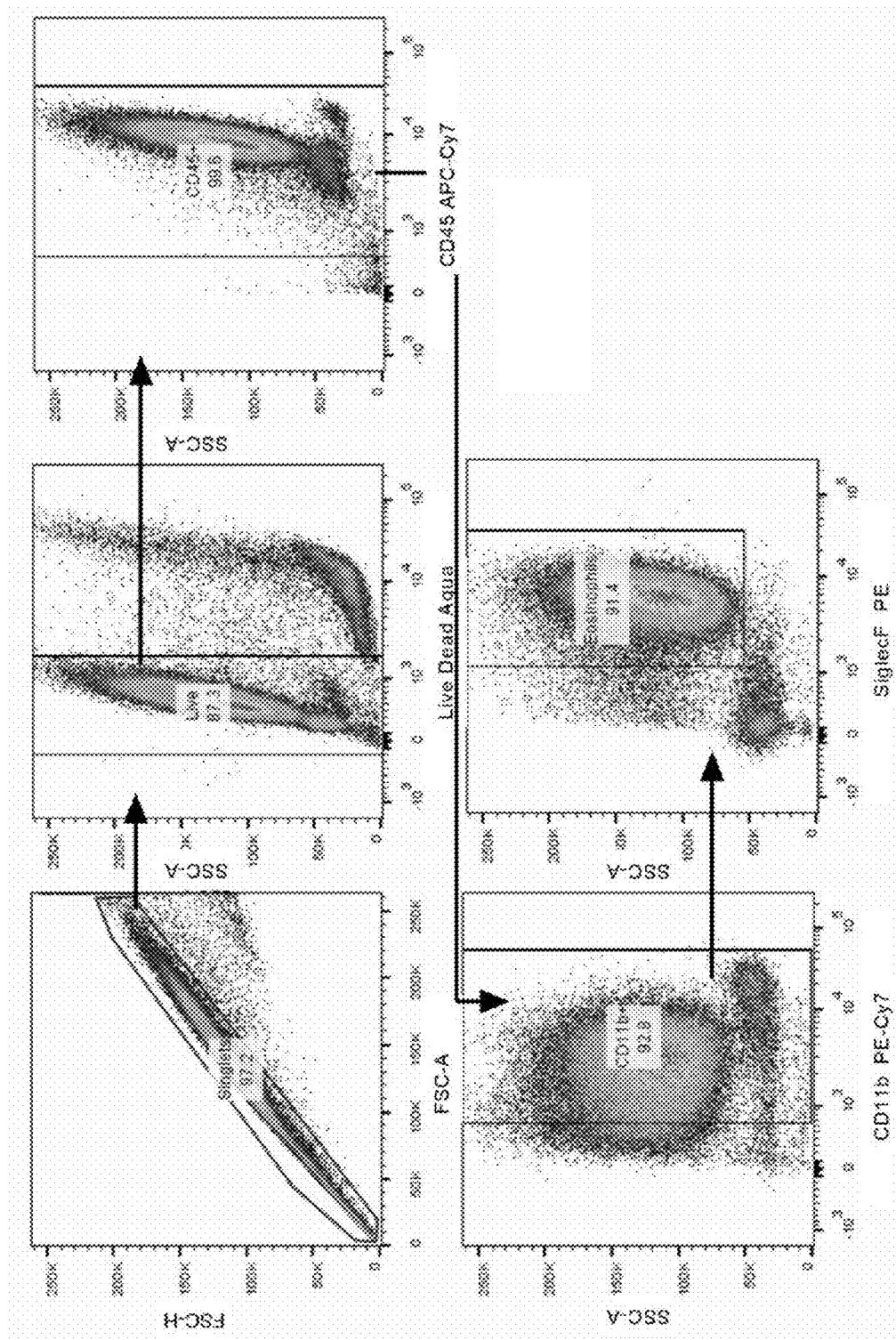
Figure 9B:
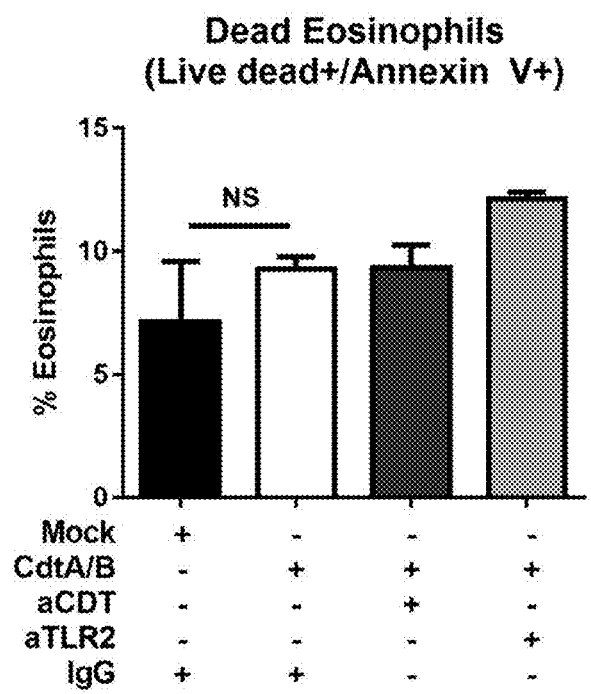
Figure 9C:
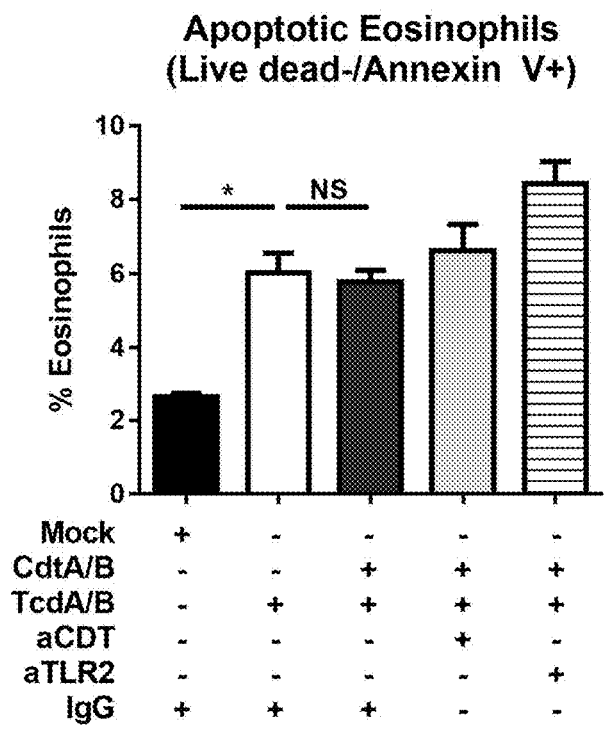
Figure 9D:
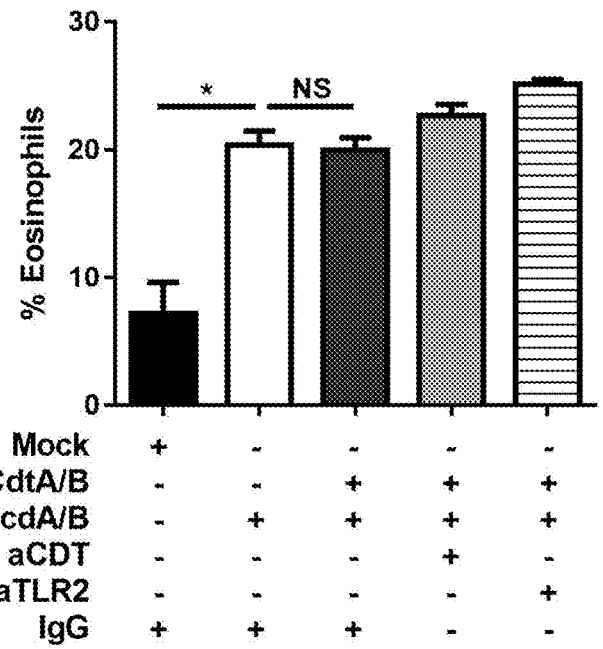

FIG. 8, comprising FIG. 8A-C (also referred to as Supplemental FIG. 3): Assessment of Th2 Cytokines and measurement of eosinophil progenitors. (FIG. 8A) Mice were sacrificed on day 3 of infection and cecal cytokines assessed in total cecal lysate by Luminex (IL-5, IL-13) or ELISA (IL-33, GM-CSF, IL-10). Values are shown normalized to total protein concentration, and are combined from two independent experiments (n=7). (FIG. 8B) Gene expression in total cecal RNA from mice on day 3 post-infection was quantified by qRT-PCR and shown normalized to GAPDH as a housekeeping gene, data shown combined from two independent experiments, (n=7). (FIG. 8C) Eosinophil progenitors (Eops) were identified as Lin− CD34+ Sca-1− IL-5Rα+ cKit$^{in}$ cells by flow cytometry (data shown are representative of 2 independent experiments, n=6). Lineage gate consisted of TCRα, CD3c, CD49b, B220, GR1, CD11b and CD11c on the PerCP Cy5.5 channel. Data shown are representative of two independent experiments. P values determined by Mann-Whitney test (FIG. 8A, B). NS=not significant. Error bars shown represent S.E.M.

FIG. 9, comprising FIG. 9A-D (also referred to as Supplemental FIG. 4): Generation of bone marrow-derived eosinophils. (FIG. 9A) Total bone marrow was harvested from C57BL/6 knockout mice and frozen in Fetal Bovine Serum with 10% DMSO until use. Thawed cells were grown in the presence of 100 ng/mL FLT3L and 100 ng/mL SCF for 4 days. The media was then removed and fresh media, supplemented with 10 ng/mL IL-5 was added. The cells were grown an additional 6 days, with fresh media added every other day. Purity of the culture was assessed by flow cytometry on day 10. Eosinophils were identified as Live, CD45$^+$, CD11b$^+$, SiglecF$^+$ SSC$^{hi}$ cells. Data shown are representative of two independent experiments. (FIG. 9B) BM Eos were incubated for 8 hours with 200 ng/mL CDTa and 200 ng/mL CDTb in the presence or absence of anti-TLR2 neutralizing antibody (aTLR2) or anti-CDT neutralizing nanobody (aCDT). Eosinophils were stained with Live dead or Annexin V and cell death was assessed by flow cytometry, data shown are representative of 3 independent experiments assayed in duplicate. (FIG. 9C-D) BM Eos were incubated for 8 hours with 200 ng/mL CDTa and 200 ng/mL CDTb and 2 ng/mL Toxin A and 2 ng/mL Toxin B. Eosinophils were stained with Live dead or Annexin V and cell death was assessed by flow cytometry, data shown are representative of 3 independent experiments assayed in duplicate *=p value <0.05 by Mann-Whitney test. NS=not significant. Error bars shown represent S.E.M.

Figure 10A:
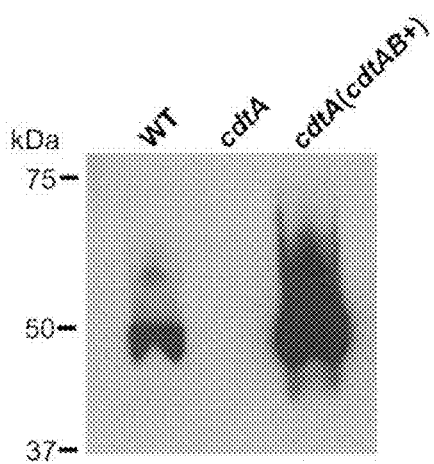
Figure 10B:
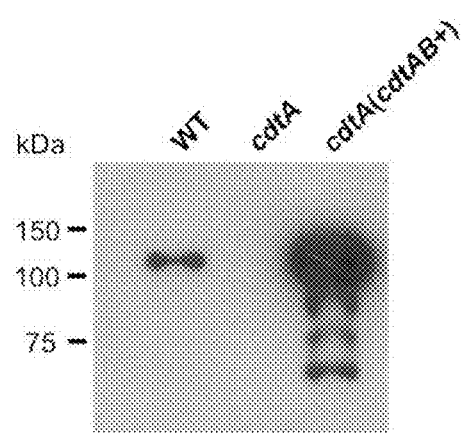

FIG. 10, comprising FIG. 10A-B (also referred to as Supplemental FIG. 5): Complementation of CDT in strain M7404. Western blot of concentrated supernatant from *C. difficile* strains M7404 (WT), M7404 CdtA− (cdtA), and M7404 CdtAComp (cdtA(cdtAB+)). Blots were probed with CDTa-specific antibody (FIG. 10A) or an antibody recognizing *Clostridium perfringens* Ib which cross-reacts with CDTb (FIG. 10B).

DETAILED DESCRIPTION

Abbreviations and Acronyms

Abx—antibiotics
aCDT—anti-CDT neutralizing nanobody
aTLR2—anti-TLR2 neutralizing antibody
BMDC—bone marrow derived dendritic cells
*C. difficile*—*Clostridium difficile*
CDI—*Clostridium difficile* infection
CDT—*C. difficile* transferase
CFU— colony forming unit
EOP—eosinophil progenitor
kg—kilogram
LSR—lipolysis stimulated lipoprotein receptor
mg—milligram
PRR— Pattern Recognition Receptor
SEAP—Secreted Embryonic Alkaline Phosphatase
siRNA—small interfering RNA
TLR2—Toll-Like Receptor 2
TSLP—thymic stromal lymphopoietin

Definitions

In describing and claiming the invention, the following terminology will be used in accordance with the definitions set forth below.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

An "agent" useful for treating a *C. difficile* infection, as used herein means any compound, molecule, or cell that can directly or indirectly be used to treat an infection. Cells can include, for example, eosinophils or one of more types of bacteria. Such an "agent" can also be referred to as a "useful agent".

As used herein, an "agonist" is a composition of matter which, when administered to a mammal such as a human, enhances or extends a biological activity attributable to the level or presence of a target compound or molecule of interest in the mammal.

As used herein, "alleviating a disease or disorder symptom," means reducing the severity of the symptom or the frequency with which such a symptom is experienced by a patient, or both. A "therapeutic" treatment is a treatment administered to a subject who exhibits signs of pathology for the purpose of diminishing or eliminating those signs.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both. A "therapeutic" treatment is a treatment administered to a subject who exhibits signs of pathology for the purpose of diminishing or eliminating those signs.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

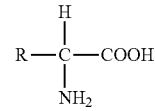

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin subunit molecules. The antibodies in the present invention may exist in a variety of forms including, for example, polyclonal antibodies, monoclonal antibodies, Fv, Fab and F(ab)2, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "secondary antibody" refers to an antibody that binds to the constant region of another antibody (the primary antibody).

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "at least two antibiotics", as used herein, means at least two different antibiotics.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands. "Binding partner," as used herein, refers to a molecule capable of binding to another molecule.

The term "biological sample," as used herein, refers to samples obtained from a subject, including, but not limited to, skin, hair, tissue, blood, plasma, serum, cells, sweat, saliva, feces, tissue and/or urine.

As used herein, the term "biologically active fragments" or "bioactive fragment" of the polypeptides encompasses natural or synthetic portions of the full length protein that are capable of specific binding to their natural ligand or of performing the function of the protein. For example, a "functional" or "active" biological molecule is a biological molecule in a form in which it exhibits a property by which it is characterized. A functional enzyme, for example, is one which exhibits the characteristic catalytic activity by which the enzyme is characterized.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Co-administer" can include simultaneous and/or sequential administration of two or more agents.

A "compound," as used herein, refers to any type of substance or agent that is can be considered a drug, or a candidate for use as a drug, as well as combinations and mixtures of the above.

The terms "comprises", "comprising", and the like can have the meaning ascribed to them in U.S. Patent Law and can mean "includes", "including" and the like. As used herein, "including" or "includes" or the like means including, without limitation.

As used herein, the term "conservative amino acid substitution" is defined herein as an amino acid exchange within one of the following five groups:

I. Small aliphatic, nonpolar or slightly polar residues:
   Ala, Ser, Thr, Pro, Gly;

II. Polar, negatively charged residues and their amides:
  Asp, Asn, Glu, Gln;
III. Polar, positively charged residues:
  His, Arg, Lys;
IV. Large, aliphatic, nonpolar residues:
  Met Leu, Ile, Val, Cys
V. Large, aromatic residues:
  Phe, Tyr, Trp "Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" generally means an amount which provides the desired local or systemic effect, such as enhanced performance. For example, an effective dose is an amount sufficient to affect a beneficial or desired clinical result. The dose could be administered in one or more administrations and can include any preselected amount. The precise determination of what would be considered an effective dose may be based on factors individual to each subject, including size, age, injury or disease being treated and amount of time since the injury occurred or the disease began. One skilled in the art, particularly a physician, would be able to determine what would constitute an effective dose.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide. The terms "fragment" and "segment" are used interchangeably herein. As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length. As used herein, the term "fragment" as applied to a nucleic acid, may ordinarily be at least about 20 nucleotides in length, typically, at least about 50 nucleotides, more typically, from about 50 to about 100 nucleotides, at least about 100 to about 200 nucleotides, at least about 200 nucleotides to about 300 nucleotides, at least about 300 to about 350, at least about 350 nucleotides to about 500 nucleotides, at least about 500 to about 600, at least about 600 nucleotides to about 620 nucleotides, at least about 620 to about 650, and or the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

As used herein, "health care provider" includes either an individual or an institution that provides preventive, curative, promotional or rehabilitative health care services to a subject, such as a patient.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

The determination of percent identity between two nucleotide or amino acid sequences can be accomplished using a mathematical algorithm. For example, a mathematical algorithm useful for comparing two sequences is the algorithm of Karlin and Altschul [50; 1990]), modified as in Karlin and Altschul [51; 1993]. This algorithm is incorporated into the NBLAST and XBLAST programs of Altschul, et al. [52], and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. [53]. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibiting TLR2" means to inhibit the activity, levels, or expression of TLR2 and is interpreted based on the context in which it is used. In one aspect, it refers to inhibiting its signaling activity by inhibiting it from binding with a ligand such as CDT. The term "inhibition of TLR2" when referring to a compound means that the compound is capable of "inhibiting TLR2".

As used herein "injecting or applying" includes administration of a compound of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide or antibody of the invention in the kit for diagnosing or effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The terms "intestinal microbiota", "gut flora", and "gastrointestinal microbiota" are used interchangeably to refer to bacteria in the digestive tract.

The term "isolated" refers to a compound, including antibodies, nucleic acids or proteins/peptides, or cell that has been separated from at least one component which naturally accompanies it.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "microbiota" refers to an assemblage of microorganisms localized to a distinct environment.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

"Pharmaceutically acceptable" means physiologically tolerable, for either human or veterinary application.

As used herein, "pharmaceutical compositions" include formulations for human and veterinary use.

"Plurality" means at least two.

As used herein, the term "prebiotic" refers to an agent that increases the number and/or activity of one or more desired bacteria. Non-limiting examples of prebiotics useful in the methods of the present invention include fructooligosaccharides (e.g., oligofructose, inulin, inulin-type fructans), galactooligosaccharides, amino acids, alcohols, and mixtures thereof.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

As used herein, the term "probiotic" refers to a substantially pure bacteria (i.e., a single isolate), or a mixture of desired bacteria, and may also include any additional components that can be administered to a mammal for restoring microbiota. Such compositions are also referred to herein as a "bacterial inoculant." Probiotics or bacterial inoculant compositions of the invention are preferably administered with a buffering agent to allow the bacteria to survive in the acidic environment of the stomach, i.e., to resist low pH and to grow in the intestinal environment. Such buffering agents include sodium bicarbonate, milk, yogurt, infant formula, and other dairy products.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

The term "reduces recurrent infection" means that the number or percentage of subjects who get another *C. difficile* infection following a course of treatment for an initial *C.*

*difficile* infection is lower compared to the number who had received standard doses or standard duration therapies.

The term "regulate" refers to either stimulating or inhibiting a function or activity of interest.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

The term "standard," as used herein, refers to something used for comparison. For example, it can be a known standard agent or compound which is administered and used for comparing results when administering a test compound or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker. Standard can also refer to a healthy individual.

A "subject" is a vertebrate, including a mammal, such as a human. Mammals include, but are not limited to, humans, farm animals, sport animals and pets.

The term "substantially pure" describes a compound, e.g., a protein or polypeptide, cell or nucleic acid that has been separated from components which naturally accompany it. Typically, a compound is substantially pure when at least 10%, including at least 20%, at least 50%, at least 60%, at least 75%, at least 90%, at least 95%, at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

As used herein, a "substantially homologous amino acid sequences" or "substantially identical amino acid sequences" includes those amino acid sequences which have at least about 92%, or at least about 95% homology or identity, including at least about 96% homology or identity, including at least about 97% homology or identity, including at least about 98% homology or identity, and at least about 99% or more homology or identity to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" or "substantially identical nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In one embodiment, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 92%, 95%, 99% or more. Substantial identity of nucleic acid sequences can be determined by comparing the sequence identity of two sequences, for example by physical/chemical methods (i.e., hybridization) or by sequence alignment via computer algorithm.

Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; preferably in 7% (SDS), 0.5 M NaPO4, 1 mM EDTA at 50° C. with washing in 1×SSC, 0.1% SDS at 50° C.; preferably 7% SDS, 0.5 M NaPO4, 1 mM EDTA at 50° C. with washing in 0.5×SSC, 0.1% SDS at 50° C.; and more preferably in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package. The default settings provided with these programs are suitable for determining substantial similarity of nucleic acid sequences for purposes of the present invention.

By the term "susceptible to *C. difficile* infection", as used herein, refers to a subject who, due to a prior disease state, treatment, or condition has now become more susceptible to such an infection than if they had not had the prior disease, treatment, or condition. Such susceptible subjects are described herein and others are also known in the art.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "treat," "treating", or "treatment" includes treating, ameliorating, or inhibiting an injury or disease related condition or a symptom of an injury or disease related condition. In one embodiment the disease, injury or disease related condition or a symptom of an injury or disease related condition is prevented; while another embodiment provides prophylactic treatment of the injury or disease related condition or a symptom of an injury or disease related condition. The term "symptom," as used herein, refers to any morbid phenomenon or departure from the normal in structure, function, or sensation, experienced by the patient and indicative of disease. In contrast, a "sign"

is objective evidence of disease. For example, a bloody nose is a sign. It is evident to the patient, doctor, nurse and other observers.

By the term "vaccine," as used herein, is meant a composition which when inoculated into a subject has the effect of stimulating an immune response in the subject, which serves to fully or partially protect the subject against a condition, disease or its symptoms. The term vaccine can encompass prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present invention provides compositions and methods for preventing and treating C. difficile infection and for inhibiting CDT induced stimulation of TLR2.

A compound of the invention can be administered once or more than once to a subject in need thereof. It can be administered once a day or at least twice a day. It can be administered once a week or more than once a week. In one aspect, a compound is administered every other day within a chosen term of treatment. In one embodiment, at least two compounds of the invention are used. In one embodiment, at least one additional therapeutic agent is administered.

One of ordinary skill in the art can determine how often to administer a compound of the invention, the duration of treatment, and the dosage to be used based on the information and teachings provided herein. Factors used in such a determination include the severity of the infection, the age and health of the subject, the particular anti-C. difficile or anti-TLR2 compound being administered, and the route of administration.

Treatment of CDI as described herein is useful for prevention of relapse or reinfection, as well as reducing the frequency of relapse or reinfection.

When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. For example, the two compounds could be administered up to 10 minutes apart, up to 30 minutes apart, up to 1 hour apart, etc. In one aspect, one or more of the compounds can be administered more than once. In one aspect, a compound is administered at least twice. In another aspect, a compound is administered at least five times. In one aspect, the method is useful for low dose treatment. In one aspect, the method is useful for short-term treatment.

In one embodiment, an effective dose as described herein is, in one aspect, one that is sufficient to prevent treat infection and control diarrhea and weight loss in a subject infected with C. difficile. Moreover, with this strategy, in one aspect, the intestinal gut flora is preserved and recurrent disease is prevented.

In one aspect, an effective dose reduces mortality.

In one aspect, the compositions and methods of the invention are useful for preventing relapse in an already treated subject and in preventing reinfection.

In one aspect, doses are preventive.

In one embodiment, a therapeutic dose of an antibody of the invention, including, but not limited, monoclonal antibodies, chimeric antibodies, humanized antibodies, various kinds of fragments, and biologically active homologs and fragments thereof, ranges from about 0.1 mg/dose to about 5,000 mg/dose. In one aspect, the dose is from about 0.1 mg to about 2,000 mg. In one aspect, the dose is from about 0.5 mg to about 2,000 mg. In one aspect, the dose is from about 0.5 mg to about 1,000 mg. In one aspect, the dose is from about 1.0 mg to about 800 mg. In another aspect, the dose is from about 2.0 mg to about 700 mg. In another aspect, the dose is from about 3.0 mg to about 600 mg. In yet another aspect, the dose is from about 4.0 mg to about 500 mg. In yet another aspect, the dose is from about 5.0 gm to about 400 mg. In a further aspect, the dose is from about 10.0 mg to about 300 mg. In another aspect, the dose is from about 15 mg to about 200 mg. In another aspect, the dose is from about 20 mg to about 100 mg. In another aspect, the dose is from about 0.1 mg to about 50 mg, or about 1 mg to about 100 mg, or about 2 mg to about 200 mg. Doses can include, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 1,000, 2,000, 3,000, 4,000, and about 5,000 mg.

Doses can also be administered based on body weight, for example at a dosage ranging from about 0.1 mg/kg body weight to about 1,000 mg/kg or about 1.0 mg/kg to about 1,000 mg/kg. In another aspect, the range is about 0.1 mg/kg to about 500 mg/kg. In another aspect, the range is about 0.1 mg/kg to about 100 mg/kg. In another aspect, the range is about 0.2 mg/kg to about 500 mg/kg. In yet another aspect, the range is from about 1.0 mg/kg to about 500 mg/kg. In yet another aspect, the range is from about 1.0 mg/kg to about 50 mg/kg. In another aspect, the range is from about 5.0 to about 100 mg/kg. In another aspect, the range is from about 5.0 to about 75 mg/kg. In another aspect, the range is from about 5.0 to about 50 mg/kg. In another aspect, the range is from about 5.0 to about 40 mg/kg. Doses can be, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, and 100 mg/kg body weight.

One of ordinary skill in the art can determine the best route of administration of a pharmaceutical composition of the invention. For example, administration can be direct, enteral, or parenteral. Enteral includes, for example, oral and rectal administration. Parenteral includes, for example, intravenous administration.

The present invention further encompasses the use of therapeutically active homologs, analogs, and derivatives of the useful compounds of the invention.

The present invention further provides for the use of a unit dose.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" unless stated otherwise.

In one embodiment, at least one compound of the invention can be administered in conjunction with another therapeutic agent. Additional therapeutic agents include, for example, antibiotics, anti-diarrheals, steroids, anti-inflammatories, other antimicrobials, and inducers of chemokines. In one aspect, more than one therapeutic agent can be administered in conjunction with a therapeutic compound of the invention. Other antimicrobials include those drugs useful against infection other than a $C.$ $diff.$ infection where a subject may have need for treatment against an additional infection as well.

The present invention further provides kits comprising compounds of the invention, an applicator, and an instructional material for the use thereof.

In one aspect, the microbiota comprises gastrointestinal microbiota.

In one aspect, the probiotic of the invention comprises at least one of $Helicobacter$ $pylori$, a $Lactobillus$ species, an $Oxalobacter$ species, $Clostridium$ $scindens$, $C.$ $populati$, $C.$ $vincentii$, $C.$ $irregulare$, $Blautia$ $hansenii$, $Eubacterium$ $contortum$, $Ruminococcus$ $torques$, $Pseudoflavonifractor$ $capillosus$, $Anaerostipes$ sp., $Staphylococcus$ $warneri$, $Lactobacillus$ $reuteri$, $Enterococcus$ $hirae$, $Enterorhabdus$ sp. $nov.$, and $Bacteroidetes$ sp. $nov.$ In one aspect, the probiotic composition comprises one or more bacteria isolated from microbiota.

In one aspect, when the agent to be administered is bacteria, the bacteria are administered in an effective amount wherein the amount is sufficient to achieve colonization of the gastrointestinal tract.

In one aspect, the bacteria are administered as an inoculant selected from the group consisting of about $1 \times 10^3$, $10^4$, $10^5$, $10^6$, $10^7$, $10^8$, $10^9$, and $10^{10}$ CFU. In one aspect, the bacteria are selected from the group consisting of $Helicobacter$ $pylori$, a $Lactobillus$ species, an $Oxalobacter$ species, $Clostridium$ $scindens$, $C.$ $populati$, $C.$ $vincentii$, $C.$ $irregulare$, $Blautia$ $hansenii$, $Eubacterium$ $contortum$, $Ruminococcus$ $torques$, $Pseudoflavonifractor$ $capillosus$, $Anaerostipes$ sp., $Staphylococcus$ $warneri$, $Lactobacillus$ $reuteri$, $Enterococcus$ $hirae$, $Enterorhabdus$ sp. $nov.$, and $Bacteroidetes$ sp. $nov.$ In one embodiment, the treatment comprises administering a conditional lethal bacterial strain.

In one embodiment, when prebiotic is used it is selected from the group consisting of fructooligosaccharides, galactooligosaccharides, amino acids, alcohols, and mixtures thereof. In one aspect, the fructooligosaccharide is selected from the group consisting of oligofructose, inulin, and inulin-type fructans.

Antimicrobials are substances that kill or inhibit the growth of microorganisms such as bacteria, fungi, virus or protozoans. Antimicrobial drugs either kill microbes (microbiocidal) or prevent the growth of microbes (microbiostatic).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices. For example the, the active compound can be formulated so as to release only in the intestine and/or the colon.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compounds of invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary with the route of administration, the nature of the condition being treated and the age and condition of the patient and will be ultimately at the discretion of the attendant physician or clinician.

Diarrhea

Inflammatory diarrhea occurs when there is damage to the intestinal mucosal lining or brush border, which leads to a passive loss of protein-rich fluids, and a decreased ability to absorb these lost fluids. Features of all three of the other types of diarrhea can be found in this type of diarrhea. It can be caused by bacterial infections, viral infections, parasitic infections, or autoimmune problems such as inflammatory bowel diseases. It can also be caused by tuberculosis, colon cancer, and enteritis.

Inflammatory diarrheas include those caused by enteric pathogens including, but not limited to, *Campylobacter jejuni*, *Salmonella species*, *Shigella species*, *Escherichia coli* (including enterohemorrhagic, enterotoxigenic, enteroaggregative *E. coli*), *Entamoeba histolytica*, *Clostridium difficile*, *Cryptosporidium* and those that have no clearly defined infectious agent such as, Crohn's Disease (CD) and ulcerative colitis (UC).

*Clostridium difficile* antibiotic-associated colitis is an increasing problem in health-care associated diarrhea, made more so recently by the emergence of a quinolone-resistant hyper-virulent strain. The infection is potentially fatal, difficult to treat, and prone to relapse.

Infectious diarrhea or contagious diarrhea may be defined as diarrhea caused by an infection of the digestive system by a bacterium, virus, or parasite that result in frequent bowel motions producing liquid feces. Viral diarrheas include, but are not limited to, those caused by Norovirus, Rotavirus, Adenovirus, or Astrovirus. Bacterial diarrheas, including diarrheas caused by their toxins, include, but are not limited to, diarrhea caused by *Campylobacter jejuni*, *Salmonella*, *Shigella*, *Vibrio cholerae*/Cholera, *Vibrio parahaemolyticus*, *Escherichia coli* (including enterohemorrhagic, enterotoxigenic, enteroaggregative *E. coli*), *Clostridium difficile*, staphylococcal toxin and *Bacillus cereus*.

Aptamers

The present invention is also directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub.

No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable sub-domains (15-50 amino acids long). This technology can be integrated with high throughput screening techniques such as phage display and reverse yeast two-hybrid traps.

The present application discloses compositions and methods for regulating the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methyl-phosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH2-S-CH2$), diinethylene-sulfoxide ($-CH2-SO-CH2$), dimethylene-sulfone ($-CH2-SO2-CH2$), 2'-O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified. The term nucleic acid also specifically includes nucleic acids composed of bases other than the five biologically occurring bases (adenine, guanine, thymine, cytosine and uracil).

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

When used in vivo for therapy, the antibodies of the invention are administered to the subject in therapeutically effective amounts (i.e., amounts that have a desired therapeutic effect). In one aspect, they will be administered parenterally.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($-NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamic, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Antibodies and their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

In one embodiment, antibodies, or antisera, directed against TLR2 or a homolog or fragment thereof, are useful for blocking the activity of TLR2.

Fragments of TLR2 may be generated and antibodies prepared against the fragments. Assays are provided herein to determine whether an antibody directed against SAS1R, or a fragment thereof, have the ability to detect TLR2, to inhibit TLR2 activity, or regulate TLR2 function.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, Immunology Today 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In one embodiment, the monoclonal antibodies described herein and the hybridomas making the antibodies, as well as those not described herein, will be deposited with the American Type Culture Collection (10801 University Boulevard, Manassas, Va. 20110-2209) and assigned Accession Numbers. The deposits will be maintained under the terms of the Budapest Treaty on the International Recognition of the Deposit of Microorganisms for the Purposes of Patent Procedure and made available for use under those terms. This assures maintenance of a viable culture of the deposit for 30 years from the date of deposit. The deposits will be made available by ATCC under the terms of the Budapest Treaty, and subject to an agreement between the University of Virginia and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC section 122 and the Commissioner's rules pursuant thereto (including 37 CFR section 1.14 with particular reference to 886 OG 638). The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws. Nucleic acid and amino acid sequences will be deposited with GenBank and made accessible to the public.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of TLR2 polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxycarbonyl as the α-amino protecting group, and the FMOC method which utilizes 9-fluorenylmethyloxycarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, C8- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As used herein, an antagonist or inhibiting agent may comprise, without limitation, a drug, a small molecule, an antibody, an antigen binding portion thereof or a biosynthetic antibody binding site that binds a particular target protein; an antisense molecule that hybridizes in vivo to a nucleic acid encoding a target protein or a regulatory element associated therewith, or a ribozyme, aptamer, or small molecule that binds to and/or inhibits a target protein, or that binds to and/or inhibits, reduces or otherwise modulates expression of nucleic acid encoding a target protein.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

When used in vivo for therapy, the antibodies of the subject invention are administered to the subject in therapeutically effective amounts (i.e., amounts that have desired therapeutic effect). They will normally be administered parenterally. The dose and dosage regimen will depend upon the degree of the infection, the characteristics of the particular antibody or immunotoxin used, e.g., its therapeutic index, the patient, and the patient's history. Advantageously the antibody or immunotoxin is administered continuously over a period of 1-2 weeks. Optionally, the administration is made during the course of adjunct therapy such as antimicrobial treatment, or administration of tumor necrosis factor, interferon, or other cytoprotective or immunomodulatory agent.

For parenteral administration, the antibodies will be formulated in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The antibodies will typically be formulated in such vehicles at concentrations of about 1.0 mg/ml to about 10 mg/ml.

Use of IgM antibodies can be preferred for certain applications; however, IgG molecules by being smaller can be more able than IgM molecules to localize to certain types of infected cells.

There is evidence that complement activation in vivo leads to a variety of biological effects, including the induction of an inflammatory response and the activation of macrophages (Unanue and Benecerraf, Textbook of Immunology, 2nd Edition, Williams & Wilkins, p. 218 (1984)). The increased vasodilation accompanying inflammation can increase the ability of various agents to localize. Therefore, antigen-antibody combinations of the type specified by this invention can be used in many ways. Additionally, purified antigens (Hakomori, Ann. Rev. Immunol. 2:103, 1984) or anti-idiotypic antibodies (Nepom et al., Proc. Natl. Acad. Sci. USA 81: 2864, 1985; Koprowski et al., Proc. Natl. Acad. Sci. USA 81: 216, 1984) relating to such antigens could be used to induce an active immune response in human patients.

The antibody compositions used are formulated and dosages established in a fashion consistent with good medical practice taking into account the condition or disorder to be treated, the condition of the individual patient, the site of delivery of the composition, the method of administration, and other factors known to practitioners.

The present application discloses compositions and methods for inhibiting the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides, as well as the protein itself and fragments thereof.

The present invention further encompasses the identification of functional fragments for the use of TLR2 for use as antigens for therapeutic antibodies as well as its use as an immunogen and as an anticancer vaccine.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

In accordance with one embodiment, a method of treating a subject in need of treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

In one embodiment, the pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 µg to about 100 g per kilogram of body weight of the subject. While the precise dosage administered will vary depending upon any number of factors, including, but not limited to, the type of animal and type of disease state being treated, the age of the subject and the route of administration. In one aspect, the dosage of the compound will vary from about 1 mg to about 10 g per kilogram of body weight of the subject. In another aspect, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the subject, etc.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Examples

The present application is based on a draft manuscript that has since published as Cowardin et al., 2016, *Nature* Microbiology, 1:8:16108, doi:10.1038/nmicrobiol.2016.108, "The binary toxin CDT enhances *Clostridium difficile* virulence by suppressing protective colonic eosinophilia".

CDT Production Enhances the Virulence of PCR-Ribotype 027 *C. difficile*

In order to test the role of CDT in pathogenesis, we infected mice with the PCR-ribotype 027 strain R20291 or one of the isogenic mutants R20291 CdtB− (lacking the binding component of CDT) or R20291 CdtA− (lacking the enzymatic component of CDT)[28,30]. Infection with R20291 led to significantly more mortality and greater weight loss than infection with an equivalent dose of R20291 CdtA− or CdtB− (60% survival vs 100% survival, n=14, p=0.001, FIG. 1A-B, Supplemental FIG. 1A-C). By day 3 of infection, mice infected with the CDT mutant strains began to recover weight and showed decreased clinical signs, while at the same time point, groups infected with R20291 displayed increased weight loss and a high mortality rate. Thus, we concluded that the mutants lacking CDT were significantly attenuated at this dose.

We confirmed this phenotype in a second PCR-ribotype 027 strain, M7404, using an isogenic mutant lacking CdtA (M7404 CdtA−) as well as a third, CdtA complemented strain (M7404 CdtAComp)[29]. Although we initially utilized a wide range of infectious doses ($1\times10^5$-$1\times10^7$ CFU/mouse) in an attempt to determine an LD50 inoculum, infection with M7404 did not result in significant mortality in our model. However, we did observe differences in weight loss and clinical scores between the groups. We found that M7404 CdtA− caused significantly less weight loss and lower disease severity scores on days 2 and 3 of infection than either the wild type or CDT complemented strains (FIG. 1C-1D). These data suggest that although M7404 and R20291 may inherently differ in virulence in this model, CDT was able to enhance disease severity in both strains.

Figure 1E:
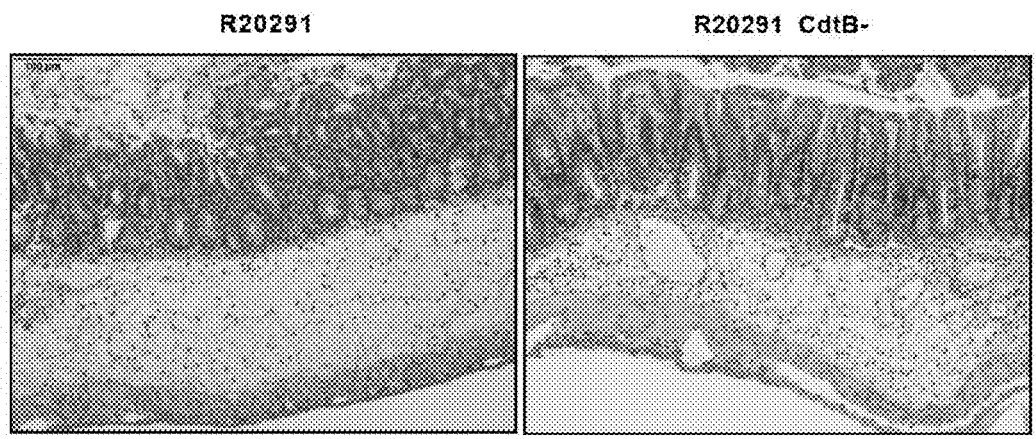
Figure 1F:
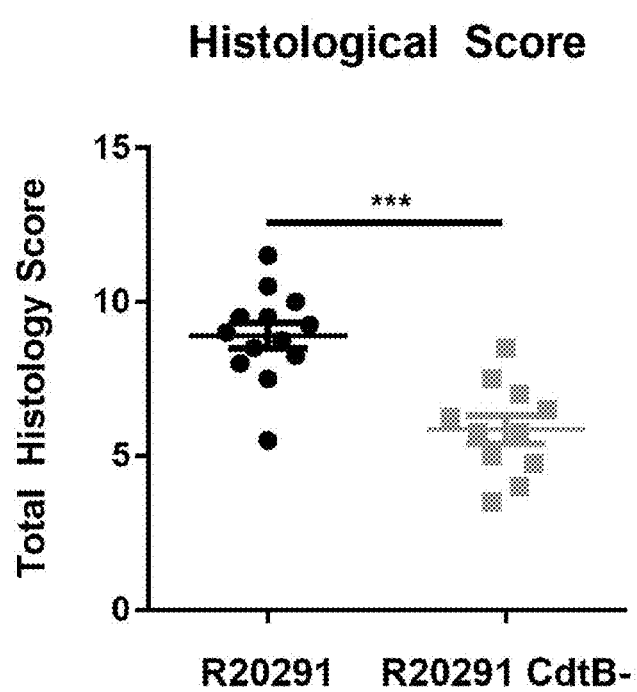

To further characterize the differences in disease manifestation in the presence or absence of CDT, we focused on strain R20291 as a model of severe *C. difficile* infection due to its significant mortality. The R20291 CdtB− mutant was chosen as a comparison to eliminate any potential effects of the known pore forming ability of CdtB alone[18]. We examined haematoxylin and eosin stained histopathological sections of the ceca from both groups (FIG. 1E-F). Sections taken from mice infected with R20291 displayed significantly more overall tissue damage in the form of epithelial barrier disruption (characterized by disorganization and sloughing of epithelial cells), submucosal edema, and lumenal exudate than those infected with R20291 CdtB− (Supplemental FIG. 1D). We next measured the production of Toxins A and B in these mice on day 3 of infection, as differential expression of these major virulence factors could explain the differences observed in tissue pathology. However, we did not observe differences in production of Toxins A and B (Supplemental FIG. 1E), suggesting that the difference in mortality rates was driven by other factors. We also assessed *C. difficile* burden in cecal contents on day 3 of infection, but did not observe a difference at this time point (Supplemental FIG. 1F). We next assessed translocation of commensals from the gut to other organs as a possible consequence of epithelial damage. This process has been suggested to drive mortality in some models of CDI[25]. However, we did not observe differences in translocation of commensals to the liver or spleen (Supplemental FIG. 1G). We conclude that tissue pathology due to CDT may influence disease outcome independent of Toxin A and B production, C. difficile burden, or liver commensal burden.

CDT Causes Increased Inflammation

Based on clinical data demonstrating a correlation between the host inflammatory response and disease severity, we hypothesized that a systemic inflammatory response could result from increased tissue pathology and contribute to mortality during infection with R20291. To investigate this possibility, we quantified the inflammatory cytokines IL-1β and IL-6 within cecal tissue of C57BL6 mice infected with R20291 or R20291 CdtB- on day 3 post infection. Both IL-1β and IL-6 are known to be highly upregulated during CDI and to influence the type of immune response which develops. We found that R20291 induced significantly more cecal IL-1β and IL-6 than R20291 CdtB- (FIG. 2A-B). Similarly, we observed significantly elevated serum IL-6 in R20291 infected mice (FIG. 2C). These results suggest that CDT production by R20291 results in a stronger local and systemic inflammatory response within the murine host.

We next sought to determine how CDT signaling directly influences inflammatory cytokine production. To investigate this, we exposed bone marrow derived dendritic cells (BMDCs) generated from C57BL6 mice to purified CDT in the presence or absence of 2 ng/mL Toxins A and B, and measured the amount of IL-1β secreted into the culture medium after 24 hours as a readout of inflammatory cytokine production (FIG. 2D). As we and other groups have shown previously, Toxins A and B are sufficient to activate the inflammasome at this concentration, but a prior "priming" signal is required for robust IL-1β secretion[27]. We found that CDT alone did not induce IL-1β secretion at this relatively long time point, even at a much higher concentration than Toxins A and B (200 ng/mL). However, CDT did enhance IL-1β release in the presence of Toxins A and B. These data suggest that CDT acts as a priming signal prior to inflammasome activation by Toxins A and B. To investigate this further, we examined the ability of CDT to activate NFκB in a RAW macrophage reporter cell line. CDT alone was able to significantly activate NFκB over mock treated cells (FIG. 2E). Additionally, CDT alone induced significant pro-IL-1b gene expression in C57BL6 BMDCs at 8 hours as measured by qRT-PCR (FIG. 2F). In order to determine whether this phenotype was specific to CDT activity, we utilized anti-CDT targeted nanobodies which have previously been demonstrated to block CDT intoxication[31]. At concentrations of 200 ng/mL (12 nM) and 20 ng/mL (1.2 nM), the anti-CDTa and anti-CDTb nanobodies both significantly decreased the amount of IL-1β secreted by BMDCs (FIG. 2G). Thus, we conclude that exposure to CDT is sufficient to activate NFκB and enhance inflammatory cytokine production.

CDT Suppresses Protective Colonic Eosinophilia

Because cytokine production shapes the immune response by influencing cell development, recruitment, proliferation and survival, we next examined the recruitment of various effector cells to the colon by flow cytometry during murine infection with R20291 and R20291 CdtB-. As expected, neutrophils (CD45$^+$ CD11b$^+$ Ly6G$^+$ Ly6C$^+$) dominated the innate compartment of both infected groups, representing roughly 20% of live cells in the colon (FIG. 3A-C). Monocytes (CD45$^+$ CD11b$^+$ Ly6C$^{hi}$ Ly6G$^-$) were also significantly elevated in the colon of both infected groups compared to uninfected, antibiotic treated controls. However, no difference was observed between neutrophils and monocytes in R20291 versus R20291 CdtB- infected groups, either as a percentage of live cells or by total cell number, suggesting that differences in neutrophil and monocyte recruitment were not responsible for differences in survival. In contrast, eosinophils were significantly elevated in R20291 CdtB- infected mice compared to R20291 infected animals (FIG. 3A-C). As with neutrophils and monocytes, eosinophils were significantly increased in both groups compared to uninfected, antibiotic treated controls.

Studies from our lab demonstrated a protective role for eosinophils after recombinant IL-25 administration. Because the protected, R20291 CdtB- infected group showed increased eosinophils compared to R20291, we hypothesized that high eosinophil numbers may correlate with protection from mortality. To examine this more closely, we used weight loss as a measure of disease severity and found a significant correlation between increased weight loss and lower eosinophil percentages, suggesting that eosinophils were associated with protection from disease (FIG. 3D).

We next sought to determine whether eosinophils themselves were protective, or simply associated with protection. To address this question, we depleted eosinophils in mice infected with R20291 or R20291 CdtB- using an anti-SiglecF targeted antibody which causes eosinophil apoptosis[32] (FIG. 3E, Supplemental FIG. 2). As expected, animals infected with R20291 CdtB- and treated with an isotype control antibody were relatively protected from mortality. In contrast, depletion of eosinophils with anti-SiglecF prior to and during infection with R20291 CdtB- significantly enhanced mortality. In R20291 infected mice, depletion of eosinophils did not significantly enhance mortality, perhaps because eosinophil counts are already relatively low in this group. Overall, these results demonstrate that an eosinophilic response is protective during CDI and that CDT production by a PCR-ribotype 027 strain has a suppressive effect on eosinophils in the colon which contributes to the enhanced virulence of this strain.

CDT Induces Apoptosis of Blood Eosinophils During Infection

Next, we investigated the cause of the decrease in eosinophils observed in R20291 infected mice. We hypothesized that eosinophil growth factors and recruitment signals would be decreased in the presence of CDT. However, R20291 and R20291 CdtB- infected mice demonstrated equivalent levels of the eosinophil-specific chemokines eotaxin-1 and eotaxin-2 (FIG. 4A). Eosinophil-promoting growth factors, such as IL-5, GM-CSF, IL-13, IL-33, and thymic stromal lymphopoietin (TSLP), were similar or elevated in R20291 infected mice, suggesting these factors were not responsible for the decrease in eosinophils observed in these mice (Supplemental FIG. 3A-B)[33-35].

Because the expression of CCR3, the cognate receptor for the eotaxins, has been shown to influence eosinophil recruitment[36], we hypothesized that different levels of this receptor could influence responsiveness to equivalent signals. Indeed, both CCR3+ and CCR3$^-$ eosinophils have been identified within the colon[32]. We evaluated eosinophil surface expression of CCR3 during infection with R20291 and R20291 CdtB- (FIG. 4B) by gating on CD45$^+$ CD11c$^-$ CD11b$^+$ SiglecF$^+$ cells and assessing CCR3 staining. We observed a significant decrease in the number of CCR3+ eosinophils in the colon of R20291 infected mice compared to R20291 CdtB– infected animals. These results could indicate that eosinophils in R20291 infected mice are less responsive to eotaxins, thereby impacting recruitment to the gut. However, CCR3 upregulation is also thought to be responsible for eosinophil egress from the bone marrow[37]. Therefore, a decrease in CCR3+ eosinophils could also reflect a decrease in the number of mature eosinophils in the colon due to cell death.

Figure 4D:
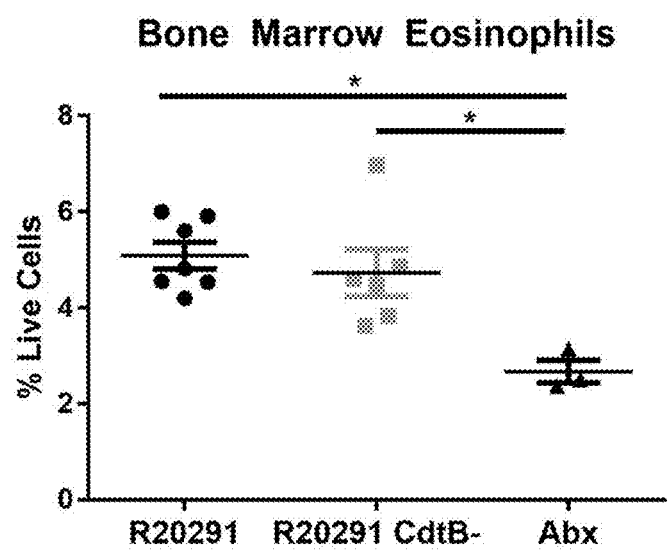
Figure 4E:
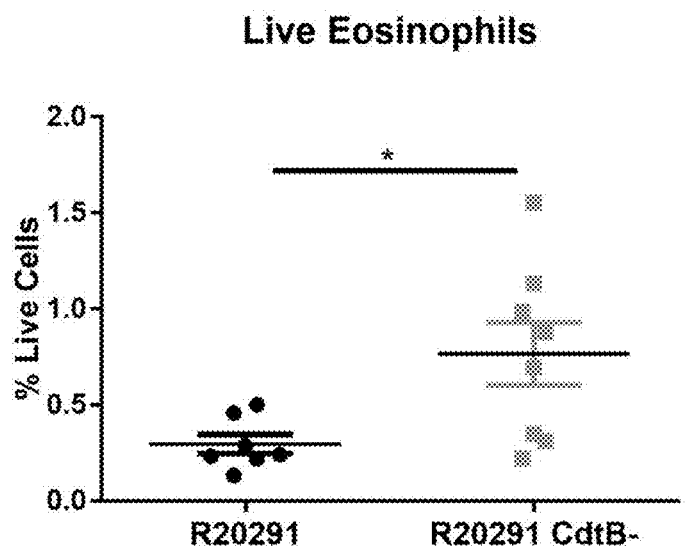

To further investigate these possibilities, we sought to determine where the eosinophil defect began. Eosinophils develop within the bone marrow from eosinophil progenitors (EoPs), defined as Lineage−, CD34+, Sca-1−, IL-5Rα+, cKit$^{int}$ cells[32,38-40] (Supplemental FIG. 3C). We did not observe a significant difference in the number of bone marrow EoPs in R20291 or R20291 CdtB– infected mice (FIG. 4C), consistent with the similar levels of eosinophil-promoting growth factors in these groups. When we examined mature bone marrow eosinophils, we noted that both infected groups had significantly more eosinophils than antibiotic treated controls (FIG. 4D). However, there was no significant difference in the number of mature eosinophils between the two infected groups. In contrast, when we examined eosinophil numbers in the peripheral blood of infected mice, we noted a significantly decreased percentage of live eosinophils in R20291 infected mice (FIG. 4E). This mirrored the phenotype observed in the colon and indicated that the eosinophil defect was systemic, but did not originate in the bone marrow, suggesting that a recruitment defect was not responsible for the observed decrease in colonic eosinophils.

Figure 4F:
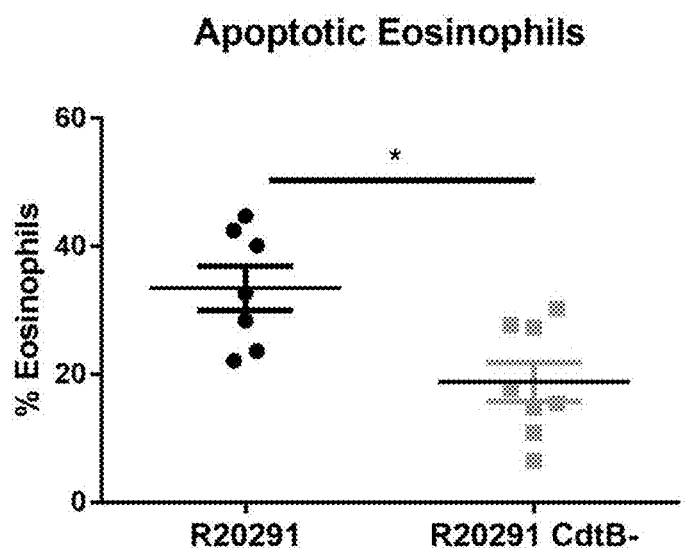

We also observed that a higher percentage of blood eosinophils in mice infected with R20291 stained positive for Annexin V, a marker of apoptosis, which could contribute to the observed defect in mature eosinophils (FIG. 4F). Taken together, these data suggest that eosinopoiesis functions similarly within both groups of infected mice, but that mature eosinophils which exit the bone marrow in R20291 infected mice undergo enhanced apoptosis, resulting in the observed decrease in live eosinophils in both the blood and colon of these animals.

CDT Recognition by TLR2 Mediates Pathogenic Eosinophil Suppression

Because activation of NFκB is classically associated with Pattern Recognition Receptor (PRR) signaling, we next asked whether these signaling pathways were involved in recognition of CDT to mediate eosinophil apoptosis. We analyzed the ability of BMDCs generated from whole bone marrow of TLR2−/−, TLR4−/−, and TLR5−/− mice to secrete IL-1β following exposure to CDT and Toxins A and B. We found that TLR2−/− BMDCs were essentially unable to respond to CDT, suggesting that this pathway may be involved in CDT recognition (FIG. 5A). To corroborate the role of TLR2, we treated wild type C57BL6 BMDCs with CDT and Toxins A and B following pre-treatment with an anti-TLR2 neutralizing antibody (anti-mTLR2-IgG, clone C9a12; catalog no. mabg-mtlr2, Invivogen) or an isotype control. The anti-TLR2 antibody significantly reduced the release of IL-1β (FIG. 5B). To determine whether this interaction occurs in vivo, we next infected TLR2−/− mice alongside C57BL/6 wild-type controls with R20291 as well as R20291 CdtB–. Mice were co-housed for 3 weeks prior to infection to equilibrate microbiota between strains. Neither TLR2−/− nor C57BL/6 mice experienced significant mortality after infection with R20291 CdtB– (FIG. 5C). However, TLR2−/− mice were significantly protected from mortality after infection with CDT-producing R20291, suggesting that TLR2 signaling enhances *C. difficile* virulence in the presence of CDT (FIG. 5C).

Figure 5D:
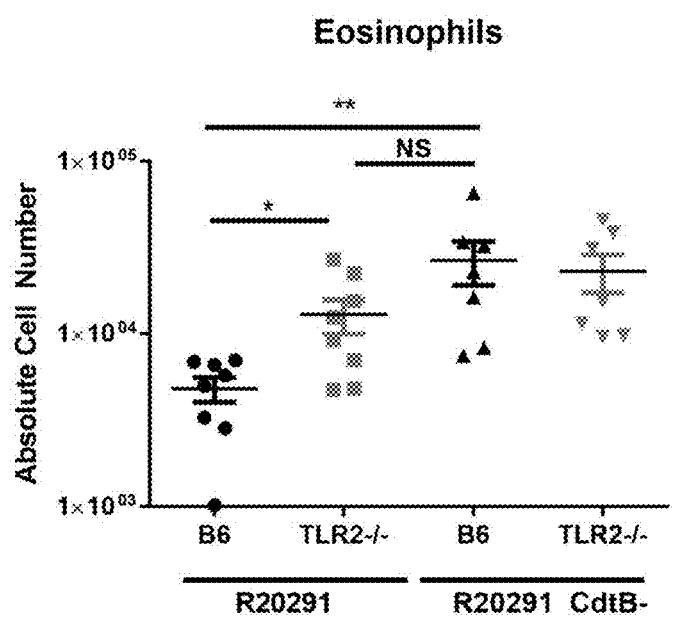
Figure 5E:
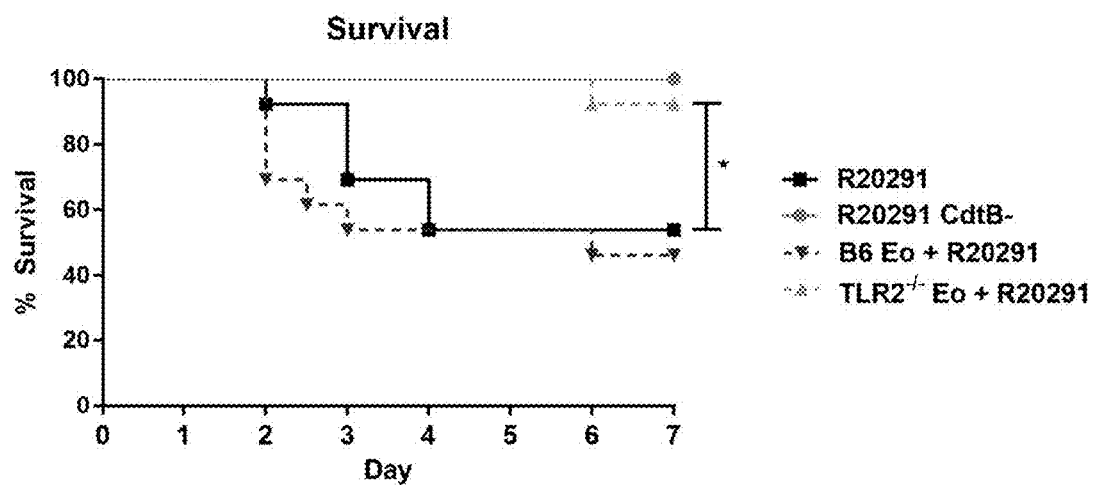
Figure 5F:
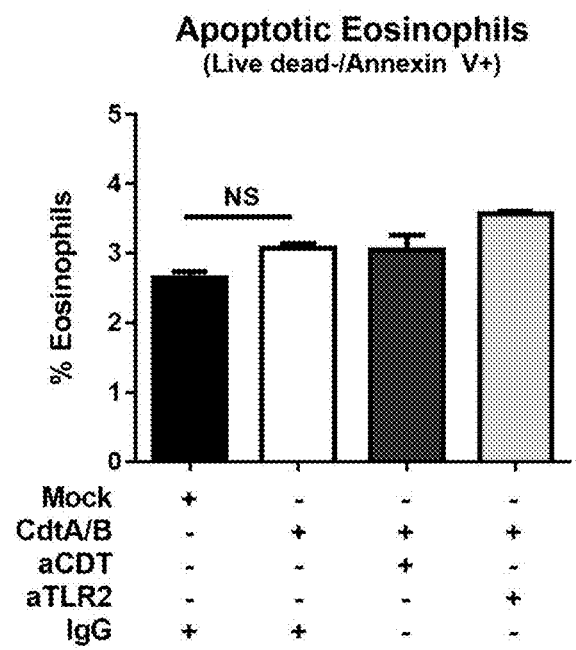
Figure 6A:
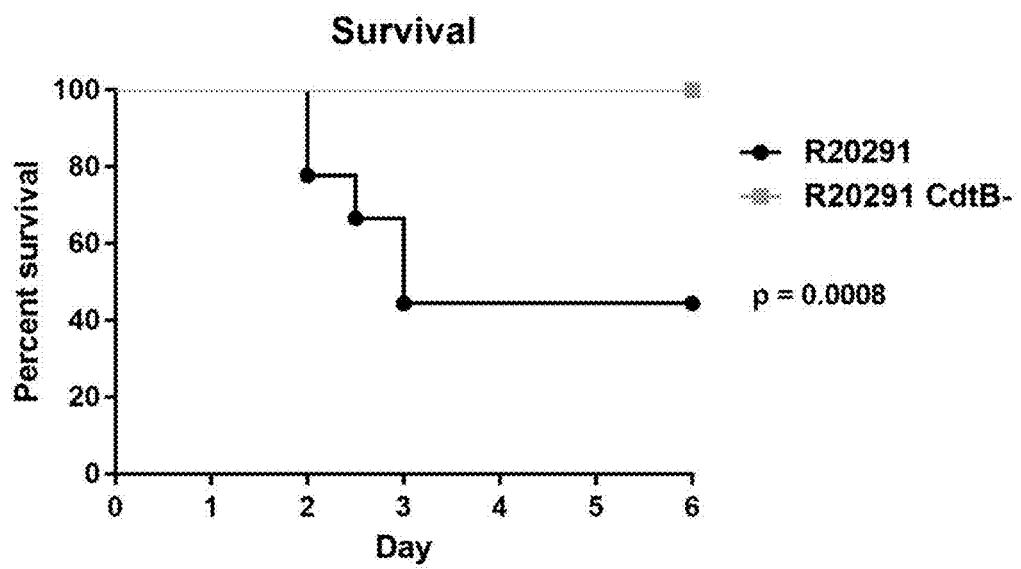
Figure 6B:
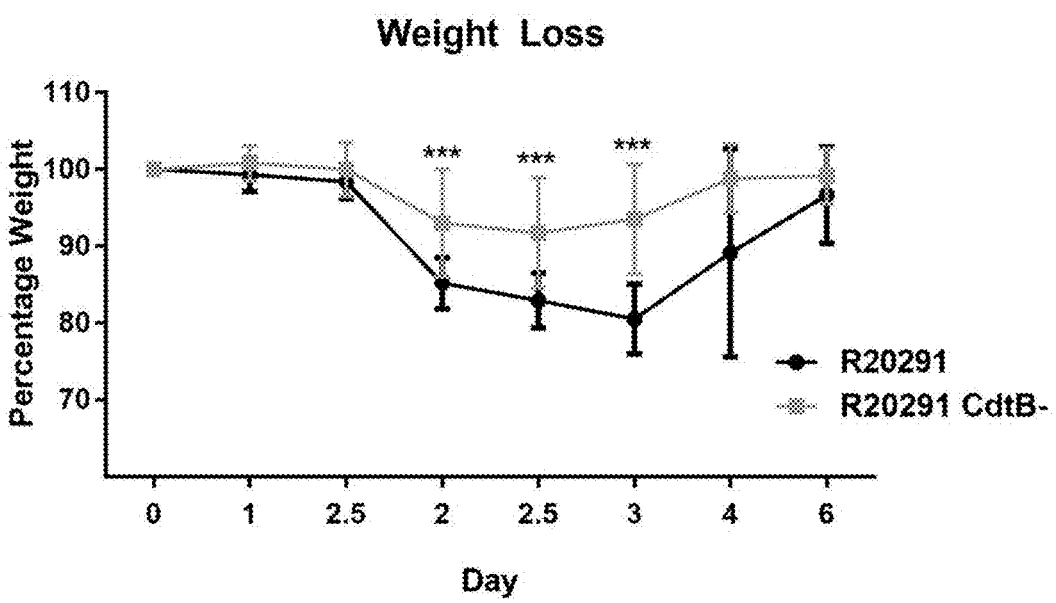
Figure 6C:
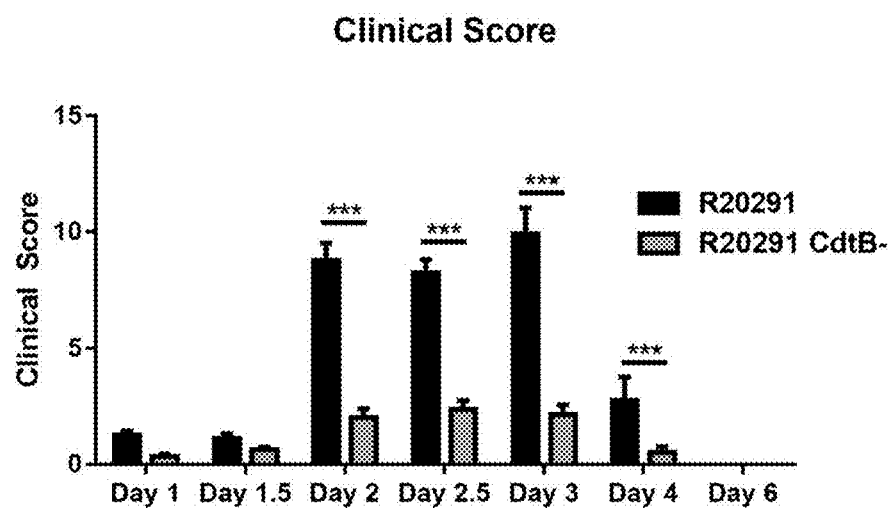
Figure 6D:
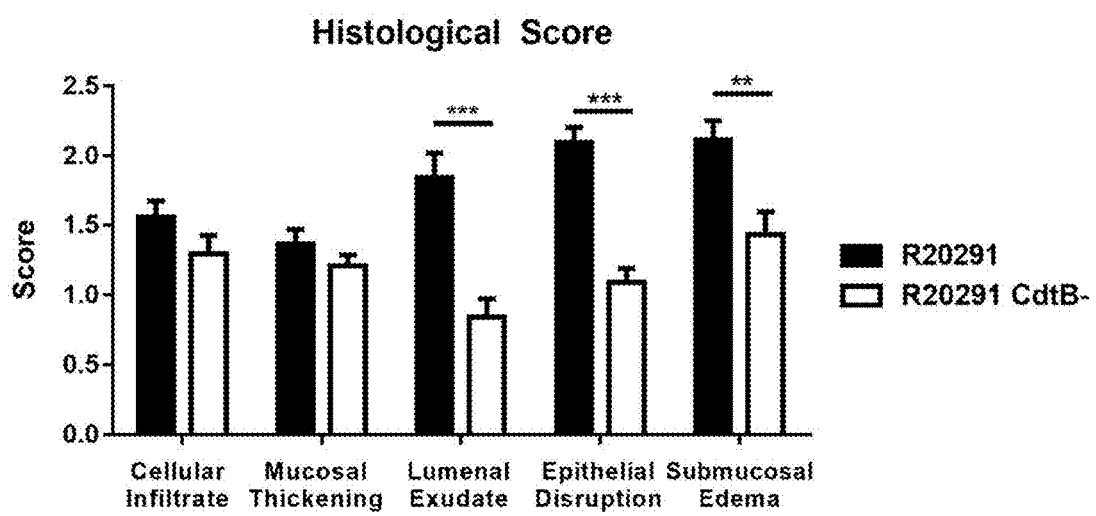
Figure 6E:
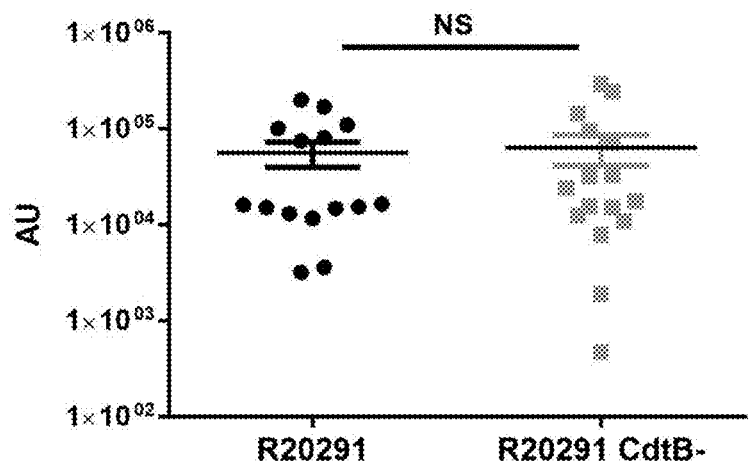
Figure 6F:
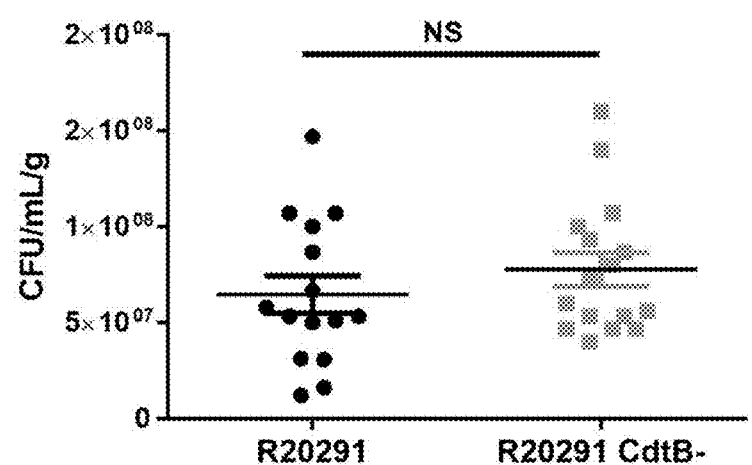
Figure 6G:
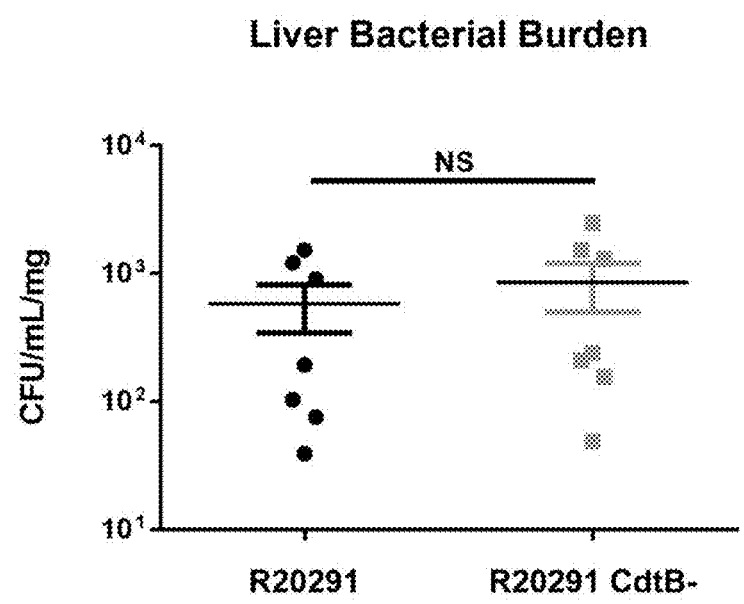

We next asked whether TLR2 may be involved in the marked decrease in colonic eosinophils observed during infection with R20291. We assessed eosinophilia in the colonic lamina propria via flow cytometry, and found that TLR2−/− mice displayed significantly higher numbers of colonic eosinophils than wild-type mice after infection with R20291. In contrast, no significant difference was noted after infection with R20291 CdtB–, suggesting that the increase in colonic eosinophils in TLR2−/− mice specifically occurred in the presence of CDT (FIG. 5D). Overall, these results suggest that recognition of CDT via TLR2 leads to enhanced systemic and local inflammation during infection, resulting in suppression of eosinophilia in the blood as well as the colon.

Restoration of TLR2−/− Eosinophils Protects Against CDT+ *C. difficile*

To determine whether preventing TLR2 signaling on a subset of eosinophils was enough to provide protection from R20291, we performed an adoptive transfer of bone marrow derived eosinophils (BM Eos) generated from either C57BL/6 or TLR2−/− mice. BM Eo cultures routinely consisted of greater than 75% CD45+ CD11b+ SiglecF+ SSC$^{hi}$ mature eosinophils (Supplemental FIG. 4A). Mice that received TLR2−/− BM Eos were significantly protected from R20291-mediated mortality compared to mice that received C57BL/6 BM Eos and to wild type controls (FIG. 5E), suggesting that restoration of eosinophils is protective only when the eosinophils are unable to recognize CDT via TLR2. We next investigated the possibility that this could be due to direct killing of eosinophils by CDT. BM Eos were incubated with CDT in vitro and cell death was assessed by Live/dead and Annexin V staining via flow cytometry. Treatment with CDT did not significantly increase the number of apoptotic (FIG. 5F) or dead eosinophils detected (Supplemental FIG. 4B). CDT likewise did not enhance apoptosis or death of eosinophils when added in conjunction with Toxins A and B (Supplemental FIG. 4C-D). Therefore, we conclude that direct killing of eosinophils by CDT is unlikely, suggesting that TLR2 signaling on eosinophils influences host survival by another mechanism, perhaps by modifying the protective function of these cells or their recruitment capability.

Methods

Bacterial Strains and Culture: *C. difficile* strains R20291 CdtA– and R20291 CdtB– was generated using the CLOSTRON system and functional inactivation of the targeted genes confirmed by Western blot as previously described[28]. Strains M7404 CdtA– and M7404 CdtComp were generated using the targetron system as previously described[29]. To prepare the infection inoculum, strains were inoculated onto BHI agar supplemented with the appropriate selective antibiotic from frozen stocks and incubated at 37° C. overnight in an anaerobic work station (Shel Labs). Single colonies were inoculated into BHI medium supplemented with cycloserine and cefoxitin (*C. difficile* supplement, Sigma) and grown anaerobically overnight at 37° C. The next day, cultures were spun for 1 minute at 6,000×g and washed twice in anaerobic PBS. The optical density of the cultures were measured and culture density adjusted to 1×10$^8$ CFU/mL (R20291 strains) or 2×10$^6$ CFU/mL (M7404 strains) in sterile, anaerobic PBS. Syringes were loaded with the inoculum and sealed in airtight bags before and during transport to the infection facility. Mice received 100 μl of inoculum each by oral gavage. To enumerate *C. difficile* in cecal samples, cecal contents were resuspended by weight in pre-reduced PBS. Resuspended cecal contents were serially diluted in PBS and plated on BHI agar supplemented with 1% Sodium Taurocholate and 1 mg/mL D-cycloserine and 0.032 mg/mL cefoxitin (Sigma) before incubating overnight anaerobically at 37° C. Liver bacterial burden was determined by homogenizing whole liver samples in sterile, aerobic PBS. Liver homogenate was serially diluted and plated on non-selective BHI agar before incubating aerobically overnight at 37° C. Liver CFU are reported according to liver sample weight.

CDT Complementation: The recombinant plasmid used for complementation of the cdtA mutant was pJIR3107, described previously[46]. C. difficile strains were grown in TY broth (3.0% tryptone, 2.0% yeast extract and 0.1% sodium thioglycollate) at 37° C. in a Don Whitley A35 Anaerobic Workstation in an atmosphere of 10% (v/v) H2, 10% (v/v) $CO_2$ and 80% (v/v) $N_2$. Toxins were partially purified and concentrated eight-fold from 72 hour C. difficile culture supernatants by methanol-chloroform precipitation[47]. Protein concentrations were determined using the BCA protein assay kit (Pierce) as per the manufacturer's instructions. Concentrated supernatant proteins (10 μg) were separated by 10% (w/v) SDS-PAGE and transferred onto a nitrocellulose membrane (Whatman). Membranes were detected as previously described[29]. CDTa and CDTb were detected using a CDTa-specific antibody and C. perfringens Ib-specific antibody that is cross reactive with CDTb[48], respectively. CDTa and CDTb antibodies were detected using horseradish peroxidase conjugated anti-rabbit goat antibodies (Millipore) The WESTERN LIGHTNING chemiluminescence reagent kit (Perkin-Elmer) was used to detect the blots, following the manufacturer's instructions and blots were recorded by exposure to X-ray film (Fujifilm).

Cell culture: Murine BMDC were generated as previously described with minor modifications[49]. Briefly, femurs and tibia were removed and bone marrow flushed with PBS. Cells were counted and viability assessed by TRYPAN BLUE staining and resuspended in RPMI 1640 media (Life Technologies) containing 10% Fetal Bovine Serum, 2 mM L-glutamine and 100 U/ml Penicillin and 100 U/ml Streptomycin. Media was supplemented with 10 ng/ml GM-CSF (Peprotech) and 55 μM β-mercaptoethanol (Gibco), and $3 \times 10^6$ cells were seeded into a T75 vent cap tissue culture flask. Cells were cultured for 7 days, and supplemented with fresh media on days 2 and 4. On day 7 cells were harvested for stimulation. For stimulation, BMDCs were detached with a cell scraper and resuspended to $1.1 \times 10^6$ cells/mL in fresh media. 180 ul of cell suspension was added per well of a 96 well plate. Cells were stimulated with the indicated concentrations of CDT or Toxins A and B in a total volume of 20 ul complete media. After the indicated incubation time, cells were spun down and supernatant removed and frozen at −80° C. for later analysis. For cell stimulation, TLR-ligand tested lipopolysaccharide (Sigma) was used as a positive control. Anti-TLR2 antibody and IgG isotype control were obtained from Invivogen and eBioscience, respectively. Anti-CDT nanobodies were generated as previously described[31].

RAW-BLUE NFκB reporter cell were obtained from Invivogen and grown in DMEM supplemented with 4.5 g/L glucose and 10% FBS. Cell responsiveness to TLR stimulation and mycoplasma status was assessed by Invivogen. For stimulation, cells were detached using a cell scraper and resuspended to a density of $5.5 \times 10^5$ cells/mL in fresh media. 180 ul of cell suspension was added per well of a 96 well plate, and cells were stimulated with CDT as indicated. Secreted Embryonic Alkaline Phosphatase (SEAP) secretion was quantified by spinning down cells, removing the culture supernatant, and incubating 50 ul of supernatant with 150 ul of Quanti-Blue detection media (Invivogen) for 30 minutes at 37° C. prior to reading in a spectrophotometer. For treatment of BM Eos with CDT, cells were harvested from culture on day 10 and plated in 96 well plates in fresh media before addition of CDT and neutralizing antibodies. Cells were harvested at 8 hours and stained for flow cytometry to assess eosinophil viability.

Toxins:

Purified CdtA and CdtB were expressed in Bacillus megaterium as previously reported[22]. CdtB was previously activated by protease cleavage (0.2 μg of trypsin/μg of protein for 30 minutes at 37° C.) prior to addition of trypsin inhibitor. Mock buffer used contained identical concentrations of trypsin and trypsin inhibitor to mimic the purified proteins. Purified Toxins A and B were purified from C. difficile strain VPI 10463 and were obtained as a kind gift from Techlab, Inc. (Blacksburg, Va.). Toxins were detected within cecal contents using the C. difficile TOXA/B ELISA according to manufacturer instructions, also kindly donated by Techlab, Inc.

Cytokine Detection:

IL-1β and IL-6 were detected in protein supernatants from BMDCs, serum and tissue lysates using the Mouse IL-1β and IL-6 READY-SET-GO! ELISA kit (eBioscience) according to manufacturer's instructions. Eotaxin-1 and Eotaxin-2 were detected in cecal lysates using R&D Systems DUOSET ELISA kits according to manufacturer's instructions. BMDC pro-IL-1β production was assessed by quantitative reverse transcription PCR. RNA was isolated using the RNEASY isolation kit (Qiagen). Contaminating genomic DNA was digested using the TURBO DNA-FREE kit (Ambion) and RNA reverse transcribed with the TETRO cDNA synthesis kit (Bioline) according to manufacturer instructions. The resulting cDNA was purified using Qiagen's PCR purification kit. IL-1b gene expression was quantified by QUANTITECT Primer assay (Qiagen) using SENSIFAST SYBR & Fluorescein Mix (Bioline) using the QUANTITECT 2-step amplification protocol. Gene expression was normalized to the S14 housekeeping gene (forward primer—see Cowardin et al., 2016; reverse primer—see Cowardin et al., 2016).

Mice and Infection:

Experiments were carried out using sex matched 8-12 week old mice. Experiments contained no fewer than 4 mice, with a goal of 8 mice, per experimental group. Based on an expected protection from 50% to 0% mortality, 6 mice per group will have >90% power to detect a statistically significant difference in mortality. All animals were housed under specific pathogen free conditions at the University of Virginia's animal facility and procedures were approved by the Institutional Animal Care and Use Committee at the University of Virginia. No animals were excluded from the study, and sample harvesting was randomized between groups. Blinded scoring of animals was not possible due to separate equipment used to prevent contamination between C. difficile strains. Mice were infected using a modified version of a previously published model for CDI[30]. Briefly, mice were given an antibiotic cocktail consisting of 45 mg/L Vancomycin (Mylan), 35 mg/L Colistin (Sigma), 35 mg/L Gentamicin (Sigma), 215 mg/L Metronidazole (Hospira) ad libitum for 3 days (Days −6 to −4). Mice were then switched back to regular drinking water for two days (Days −3 onward), followed by an IP injection (0.032 mg/g) of Clindamycin (Hospira) on Day −1. On Day 0, mice were gavaged with C. difficile. Mice were monitored twice daily throughout the course of the infection and immediately euthanized if severe illness developed according to clinical scoring parameters. Scores were based on weight loss, coat condition, activity level, diarrhea, and posture and eye condition for a cumulative clinical score between 1 and 20.

Tissue Protein and Histology:

Mice were humanely euthanized and tissue was immediately removed for analysis. Total cecal lysate was generated by removing the ceca and rinsing gently with PBS. Tissue was bead beaten for 1 minute in 400 ul of Lysis Buffer I (1×HALT Protease Inhibitor (Pierce), 5 mM HEPES). 400 ul of Lysis Buffer II was added (1×HALT Protease Inhibitor (Pierce), 5 mM HEPES, 2% TRITON X-100) and tubes inverted gently. Tissue samples were incubated on ice for 30 minutes, followed by a 5 minute spin at 13,000×g at 4° C. Supernatant was removed to a fresh tube, and total protein concentration was assessed by BCA assay according to manufacturer's instructions (Pierce). Cytokine concentration is shown relative to total protein concentration. To generate histological sections, cecal samples were placed in Bouin's Solution (Sigma) for 18 hours. Tissue samples were moved to 70% Ethanol before paraffin embedding and sectioning. Sections were mounted on slides and stained with haemotoxylin and eosin prior to microscopic examination. Slides were scored blinded, with a score from 0 to 3 assigned based on 5 parameters: epithelial disruption, submucosal edema, inflammatory infiltrate, mucosal thickening and luminal exudate as previously reported[50]. Scores were averaged between 3 independent, blinded observers.

Eosinophil Depletion:

Eosinophils were depleted using an anti-mouse SiglecF monoclonal antibody (R&D Systems) as previously shown[32]. Control groups received Rag IgG2A isotype control antibody (R&D Systems). Both groups were given 40 ug of antibody per mouse on day −1 and day +1 of infection (80 ug total per mouse) via intraperitoneal injection. Eosinophil depletion was evaluated by flow cytometry, which showed an 82% average reduction in colonic eosinophils.

Eosinophil Adoptive Transfer:

Bone marrow derived eosinophils were generated as previously described and examined on day 10 for eosinophil markers and viability via flow cytometry[51,52] Cultures routinely consisted of >75% live CD45+ CD11b+ SiglecF+ SSC$^{hi}$ eosinophils. For adoptive transfer, cultures were synchronized such that each injection occurred on day 10 of culture. Cultures were collecting using a cell scraper and washed 2× in sterile PBS. $4×10^5$ eosinophils were given intraperitoneally per mouse. Mice received 4 total injections of eosinophils, starting the day prior to infection and for 3 subsequent days.

Statistical Analysis:

Statistical analysis was calculated and significance determined (p<0.05) using Mann-Whitney test or other suitable analysis, including Welch's t-test for unequal variance. All statistical analysis was performed using GraphPad Prism software.

Flow Cytometry:

Colonic lamina propria was prepared for flow cytometry by thoroughly rinsing the tissue in Hank's Balanced Salt Solution (HBSS) supplemented with 5% FBS and 25 mM HEPES. Epithelial cells were removed by gentle shaking for 40 minutes at 37° C. in HBSS with 15 mM HEPES, 5 mM EDTA, 10% FBS and 1 mM DTT. Halfway through the incubation, colon samples were transferred to fresh buffer. Next, colon samples were thoroughly chopped using scissors and digested in RPMI 1640 containing 0.17 mg/mL LIBERASE TL (Roche) and 30 ug/mL DNase (Sigma). Samples were digested for 40 minutes at 37° C. with gentle shaking. Samples were then spun down at 300×g and resuspended in HBSS with 5% FBS and 25 mM HEPES before passage through a 100 uM cell strainer followed by a 40 uM cell strainer (both Fisher Scientific). Cells were counted and density adjusted to $1×10^7$ cells/mL. 100 ul of cell suspension were aliquoted per well of a 96 well plate for antibody staining. For staining, cells were initially blocked with TRUSTAIN FCX (anti-mouse CD16/32 antibody, BioLegend) for ten minutes at room temperature. Cells were spun down and resuspended in LIVE/DEAD Fixable Aqua (Life Technologies) for 20 minutes at room temperature. Cells were washed twice and stained with fluorochrome conjugated antibodies. Flow cytometry was performed on an LSR FORTESSA cytometer (BD Biosciences) and all data analysis performed via FLOWJO (Tree Star Inc.). See Supplemental Table S1 for antibodies used.

TABLE S1

Antibodies used for Flow Cytometry.

| Fluorochrome | Antibody | Source | Clone |
|---|---|---|---|
| Brilliant Violet 421 | CD11c | BioLegend | N418 |
| AlexaFluor 488 | CD125/IL-5Rα | BD Biosciences | T21 |
| PE | SiglecF | BD Pharmingen | E50-2440 |
| PeCy7 | CD11B | BioLegend | M1/70 |
| APC-CY7 | CD45 | BioLegend | 30-F11 |
| AlexaFluor 647 | CD193/CCR3 | BD Biosciences | 83103 |
| PerCP-Cy5.5 | Gr1 | BioLegend | RB6-8C5 |
| AlexaFluor 488 | Annexin V | Life Technologies | |
| PE | c-Kit/CD117 | BioLegend | 2B8 |
| AlexaFluor 700 | CD34 | BD Biosciences | RAM34 |
| PeCy7 | Sca-1 | BioLegend | D7 |
| PerCP-Cy5.5 | TCRβ | BioLegend | H57-597 |
| PerCP-Cy5.5 | CD3ε | BioLegend | 17A2 |
| PerCP-Cy5.5 | CD49b | BioLegend | DX5 |
| PerCP-Cy5.5 | B220 | BioLegend | RA3-6B2 |
| PerCP-Cy5.5 | CD11c | BioLegend | N418 |
| PerCP-Cy5.5 | CD11b | BioLegend | M1/70 |
| FITC | LY6C | BD Biosciences | AL-21 |
| PE-CY7 | LY6G | BD Biosciences | 1A8 |

Discussion

Despite understanding the enzymatic function of CDT, the role of this toxin in enhancing *C. difficile* virulence remains incompletely characterized, and the influence of CDT on the host immune response has not been examined. We found that CDT was able to enhance the virulence of two PCR-ribotype 027 *C. difficile* strains, resulting in increased tissue pathology. CDT skewed the host inflammatory response by suppressing protective eosinophils within the colon and blood via the indirect induction of eosinophil apoptosis. Additionally, purified CDT was able to activate NFκB and to induce inflammatory IL-1β production in conjunction with Toxins A and B. This required TLR2 signaling, and TLR2-deficient mice were protected against the CDT-producing strain R20291, correlating with increased colonic eosinophils compared to wild type mice. Finally, adoptive transfer of TLR2 deficient eosinophils was sufficient to protect mice against CDT+ R20291, demonstrating an unexpected role for eosinophils in protection.

Although we demonstrated that CDT is able to activate NFκB and enhance inflammatory cytokine production, it is unclear at which step this signaling occurs in vivo. CDT may intoxicate epithelial cells to promote recruitment of immune cells, which in turn enhance the inflammatory response. Alternatively, CDT may act directly on immune cells to enhance NFκB activation. The role of the lipolysis-stimulated lipoprotein receptor in mediating an immune response is also unknown. It is conceivable that LSR and TLR2 mediate separate pathways in response to CDT. Alternatively, these receptors may cooperate to permit CDT recognition and intoxication.

It remains unclear how CDT signaling results in apoptosis of eosinophils. Although our data suggest that CDT does not directly kill eosinophils, intoxication by CDT and the subsequent increase in inflammatory cytokine production by innate cells may shape the inflammatory environment to support eosinophil apoptosis. Indeed, innate inflammation has long been known to suppress eosinophilia by unknown mechanisms[41,42]. TLR2-dependent eosinophil suppression is also not unprecedented, as multiple groups have reported in different murine models of allergic inflammation[43-45]. Administration of a TLR2 agonist has been shown to reduce eosinophilia by inducing T cell apoptosis in a model of allergic conjunctivitis, as well as by enhancing T regulatory cells and inducing Th1 cytokines in murine asthma models. It remains to be investigated whether these mechanisms underlie eosinophil suppression during CDI. The protective role of eosinophils is likewise unknown, and clarifying how TLR2 signaling impacts the function of these cells may provide clues to their activity during infection.

Understanding the mechanism by which CDT enhances *C. difficile* virulence is essential to understanding the virulence of PCR-ribotype 027 strains, and of other hypervirulent strains which express CDT. These isolates are increasingly common and their spread likely contributes to the overall increase in CDI incidence and severity. Our data suggests that targeting CDT in the development of vaccines and therapeutic inhibitors is essential to successfully treating infected with these strains, and identifies the protective role eosinophils play during CDI. Our knowledge of *C. difficile* virulence factors which result in pathogenic immune responses during CDI continues to evolve, presenting new potential drug targets for treating this common and life threatening infection.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Lessa, F. C. et al. Burden of *Clostridium difficile* infection in the United States. *N. Engl. J. Med.* 372, 825-834 (2015).
2. Ananthakrishnan, A. N. *Clostridium difficile* infection: epidemiology, risk factors and management. *Nat. Rev. Gastroenterol. Hepatol.* 8, 17-26 (2010).
3. Kuehne, S. A. et al. The role of toxin A and toxin B in *Clostridium difficile* infection. *Nature* 467, 711-713 (2010).
4. Carter, G. P., Rood, J. I. & Lyras, D. The role of toxin A and toxin B in *Clostridium difficile*-associated disease. *Gut Microbes* 1, 58-64 (2010).
5. Lyerly, D. M., Saum, K. E., MacDonald, D. K. & Wilkins, T. D. Effects of *Clostridium difficile* toxins given intragastrically to animals. *Infect. Immun.* 47, 349-352 (1985).
6. Lee, J. Y. et al. *Clostridium difficile* toxin A promotes dendritic cell maturation and chemokine CXCL2 expression through p38, IKK, and the NF-kappaB signaling pathway. *J. Mol. Med. Berl. Ger.* 87, 169-180 (2009).
7. Bobo, L. D. et al. MK2 Kinase Contributes to *Clostridium difficile*-Associated Inflammation. *Infect. Immun.* (2012). doi:10.1128/IAI.00186-12
8. Stewart, D. B., Berg, A. & Hegarty, J. Predicting Recurrence of *C. difficile* Colitis Using Bacterial Virulence Factors: Binary Toxin Is the Key. *J. Gastrointest. Surg.* 17, 118-125 (2013).
9. Bacci, S., Mølbak, K., Kjeldsen, M. K. & Olsen, K. E. P. Binary Toxin and Death after *Clostridium difficile* Infection. *Emerg. Infect. Dis.* 17, 976-982 (2011).
10. Barbut, F. et al. Clinical features of *Clostridium difficile*-associated infections and molecular characterization of strains: results of a retrospective study, 2000-2004. *Infect. Control Hosp. Epidemiol.* 28, 131-139 (2007).
11. Rupnik, M., Wilcox, M. H. & Gerding, D. N. *Clostridium difficile* infection: new developments in epidemiology and pathogenesis. *Nat. Rev. Microbiol.* 7, 526-536 (2009).
12. Bauer, M. P. et al. *Clostridium difficile* infection in Europe: a hospital-based survey. *The Lancet* 377, 63-73 (2011).
13. Spigaglia, P. & Mastrantonio, P. Comparative analysis of *Clostridium difficile* clinical isolates belonging to different genetic lineages and time periods. *J. Med. Microbiol.* 53, 1129-1136 (2004).
14. Popoff, M. R., Rubin, E. J., Gill, D. M. & Boquet, P. Actin-specific ADP-ribosyltransferase produced by a *Clostridium difficile* strain. *Infect. Immun.* 56, 2299-2306 (1988).
15. Stiles, B. G. et al. *Clostridium* and *Bacillus* Binary Enterotoxins: Bad for the Bowels, and Eukaryotic Being. *Toxins* 6, 2626-2656 (2014).
16. Hemmasi, S. et al. Interaction of the *Clostridium difficile* Binary Toxin CDT and its Host Cell Receptor LSR. *J. Biol. Chem.* (2015). doi:10.1074/jbc.M115.650523
17. Papatheodorou, P. et al. Lipolysis-stimulated lipoprotein receptor (LSR) is the host receptor for the binary toxin *Clostridium difficile* transferase (CDT). *Proc. Natl. Acad. Sci. U.S.A* 108, 16422-16427 (2011).
18. Gerding, D. N., Johnson, S., Rupnik, M. & Aktories, K. *Clostridium difficile* binary toxin CDT. *Gut Microbes* 5, 15-27 (2014).
19. Higashi, T. et al. Analysis of the 'angulin' proteins LSR, ILDR1 and ILDR2—tricellulin recruitment, epithelial barrier function and implication in deafness pathogenesis. *J. Cell Sci.* 126, 966-977 (2013).
20. Barth, H., Aktories, K., Popoff, M. R. & Stiles, B. G. Binary Bacterial Toxins: Biochemistry, Biology, and Applications of Common *Clostridium* and *Bacillus* Proteins. *Microbiol. Mol. Biol. Rev.* 68, 373-402 (2004).
21. Schwan, C. et al. *Clostridium difficile* toxin CDT hijacks microtubule organization and reroutes vesicle traffic to increase pathogen adherence. *Proc. Natl. Acad. Sci. U.S.A* 111, 2313-2318 (2014).
22. Schwan, C. et al. *Clostridium difficile* toxin CDT induces formation of microtubule-based protrusions and increases adherence of bacteria. *PLoS Pathog.* 5, e1000626 (2009).
23. El Feghaly, R. E., Stauber, J. L., Tan, P. I. & Haslam, D. B. Intestinal Inflammatory Biomarkers and Outcome in 23. Pediatric *Clostridium difficile* Infections. *J. Pediatr.* (2013). doi:10.1016/j.jpeds.2013.07.029
24. Abt, M. C. et al. Innate Immune Defenses Mediated by Two ILC Subsets Are Critical for Protection against Acute *Clostridium difficile* Infection. *Cell Host Microbe* 18, 27-37 (2015).
25. Hasegawa, M. et al. Interleukin-22 regulates the complement system to promote resistance against pathobionts after pathogen-induced intestinal damage. *Immunity* 41, 620-632 (2014).
26. Buonomo, E. L. et al. Role of IL-23 signaling in *Clostridium difficile Colitis. J. Infect. Dis.* jit277 (2013). doi:10.1093/infdis/jit277
27. Cowardin, C. A. et al. Inflammasome activation contributes to interleukin-23 production in response to *Clostridium difficile. mBio* 6, (2015).
28. Kuehne, S. A. et al. The importance of toxin A, toxin B and CDT in virulence of an epidemic *Clostridium difficile* strain. *J. Infect. Dis.* (2013). doi:10.1093/infdis/jit426
29. Carter, G. P. et al. Defining the Roles of TcdA and TcdB in Localized Gastrointestinal Disease, Systemic Organ Damage, and the Host Response during *Clostridium difficile* Infections. *mBio* 6, e00551-15 (2015).
30. Chen, X. et al. A mouse model of *Clostridium difficile*-associated disease. *Gastroenterology* 135, 1984-1992 (2008).
31. Unger, M. et al. Selection of Nanobodies that Block the Enzymatic and Cytotoxic Activities of the Binary *Clostridium Difficile* Toxin CDT. *Sci. Rep.* 5, (2015).
32. Griseri, T. et al. Granulocyte Macrophage Colony-Stimulating Factor-Activated Eosinophils Promote Interleukin-23 Driven Chronic Colitis. *Immunity* 43, 187-199 (2015).
33. Rosenberg, H. F., Dyer, K. D. & Foster, P. S. Eosinophils: changing perspectives in health and disease. *Nat. Rev. Immunol.* 13, 9-22 (2013).
34. Jung, Y. & Rothenberg, M. E. Roles and Regulation of Gastrointestinal Eosinophils in *Immunity* and Disease. *J. Immunol.* 193, 999-1005 (2014).
35. Rådinger, M. & Lötvall, J. Eosinophil progenitors in allergy and asthma—do they matter? *Pharmacol. Ther.* 121, 174-184 (2009).
36. Sehmi, R. et al. Allergen-induced fluctuation in CC chemokine receptor 3 expression on bone marrow CD34+ cells from asthmatic subjects: significance for mobilization of haemopoietic progenitor cells in allergic inflammation. *Immunology* 109, 536-546 (2003).
37. Palframan, R. T. et al. Mechanisms of Acute Eosinophil Mobilization from the Bone Marrow Stimulated by Interleukin 5: The Role of Specific Adhesion Molecules and Phosphatidylinositol 3-Kinase. *J. Exp. Med.* 188, 1621-1632 (1998).
38. Denburg, J. A. & Keith, P. K. Eosinophil progenitors in airway diseases: clinical implications. *Chest* 134, 1037-1043 (2008).
39. Gauvreau, G. M., Ellis, A. K. & Denburg, J. A. Haemopoietic processes in allergic disease: eosinophil/basophil development. *Clin. Exp. Allergy J. Br. Soc. Allergy Clin. Immunol.* 39, 1297-1306 (2009).
40. Smith, S. G. et al. Thymic stromal lymphopoietin and IL-33 modulate migration of hematopoietic progenitor cells in patients with allergic asthma. *J. Allergy Clin. Immunol.* (2015). doi:10.1016/j.jaci.2014.12.1918
41. Bass, D. A. Behavior of eosinophil leukocytes in acute inflammation. II. Eosinophil dynamics during acute inflammation. *J. Clin. Invest.* 56, 870-879 (1975).
42. Morgan, J. E. & Beeson, P. B. Experimental Observations on the Eosinopenia Induced by Acute Infection. *Br. J. Exp. Pathol.* 52, 214-220 (1971).
43. Fukushima, A., Yamaguchi, T., Ishida, W., Fukata, K. & Ueno, H. TLR2 agonist ameliorates murine experimental allergic conjunctivitis by inducing CD4 positive T-cell apoptosis rather than by affecting the Th1/Th2 balance. *Biochem. Biophys. Res. Commun.* 339, 1048-1055 (2006).
44. Nawijn, M. C. et al. TLR-2 Activation Induces Regulatory T Cells and Long-Term Suppression of Asthma Manifestations in Mice. *PLoS ONE* 8, e55307 (2013).
45. Patel, M. et al. TLR2 Agonist Ameliorates Established Allergic Airway Inflammation by Promoting Th1 Response and Not via Regulatory T Cells. *J. Immunol.* 174, 7558-7563 (2005).
46. Carter, G. P. et al. Binary Toxin Production in *Clostridium difficile* Is Regulated by CdtR, a LytTR Family Response Regulator. *J. Bacteriol.* 189, 7290-7301 (2007).
47. Mackin, K. E., Carter, G. P., Howarth, P., Rood, J. I. & Lyras, D. Spo0A differentially regulates toxin production in evolutionarily diverse strains of *Clostridium difficile. PloS One* 8, e79666 (2013).
48. Perelle, S., Gibert, M., Bourlioux, P., Corthier, G. & Popoff, M. R. Production of a complete binary toxin (actin-specific ADP-ribosyltransferase) by *Clostridium difficile* CD196. *Infect. Immun.* 65, 1402-1407 (1997).
49. Gross, O. Measuring the inflammasome. *Methods Mol. Biol.* Clifton N.J. 844, 199-222 (2012).
50. Pawlowski, S. W. et al. Murine Model of *Clostridium difficile* Infection with Aged Gnotobiotic C57BL/6 Mice and a BI/NAP1 Strain. *J. Infect. Dis.* 202, 1708-1712 (2010).
51. Dyer, K. D. et al. Functionally competent eosinophils differentiated ex vivo in high purity from normal mouse bone marrow. *J. Immunol. Baltim. Md.* 1950 181, 4004-4009 (2008).
52. Wen, T., Besse, J. A., Mingler, M. K., Fulkerson, P. C. & Rothenberg, M. E. Eosinophil adoptive transfer system to directly evaluate pulmonary eosinophil trafficking in vivo. *Proc. Natl. Acad. Sci. U.S.A* 110, 6067-6072 (2013).

What is claimed is:

1. A method of treating *Clostridium difficile* (*C. difficile*) infection in a mammalian subject in need thereof by inhibiting the effects of *C. difficile* transferase (CDT), said method comprising administering to said subject a composition comprising an effective amount of an inhibitor of Toll-Like Receptor 2 (TLR2), wherein said inhibitor is an antibody that binds specifically to the TLR2 and inhibits stimulation of TLR2 activity by the CDT, thereby treating the *C. difficile* infection by inhibiting the effects of the CDT.

2. The method of claim 1, wherein the antibody is selected from the group consisting of a polyclonal antibody, a monoclonal antibody, a humanized antibody, Fv, Fab, F(ab)2, and ScFv.

3. The method of claim 1, wherein the antibody inhibits interaction of the CDT with the TLR2.

4. The method of claim 1, wherein the composition is administered before said subject is infected with said *C. difficile*.

5. The method of claim 1, wherein the composition is administered after said subject is infected with said *C. difficile*.

6. The method of claim 1, wherein the method inhibits suppression of protective colonic eosinophilia by the CDT in said subject.

7. The method of claim 1, wherein the composition comprises an additional therapeutic agent.

8. The method of claim 7, wherein said additional therapeutic agent is a nanobody that inhibits CDT, CDTa, or CDTb.

9. The method of claim 1, wherein subject is a human.

* * * * *